US012185904B2

(12) United States Patent
Iwane

(10) Patent No.: US 12,185,904 B2
(45) Date of Patent: Jan. 7, 2025

(54) ENDOSCOPE SYSTEM

(71) Applicant: FUJIFILM Corporation, Tokyo (JP)

(72) Inventor: Kosuke Iwane, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 653 days.

(21) Appl. No.: 17/372,648

(22) Filed: Jul. 12, 2021

(65) Prior Publication Data
US 2021/0338069 A1    Nov. 4, 2021

Related U.S. Application Data

(63) Continuation of application No. PCT/JP2019/047008, filed on Dec. 2, 2019.

(30) Foreign Application Priority Data

Jan. 30, 2019 (JP) ................................. 2019-014802

(51) Int. Cl.
*A61B 1/00* (2006.01)
*A61B 1/06* (2006.01)
*A61B 1/313* (2006.01)

(52) U.S. Cl.
CPC .... *A61B 1/000094* (2022.02); *A61B 1/00042* (2022.02); *A61B 1/0005* (2013.01);
(Continued)

(58) Field of Classification Search
CPC .......... A61B 1/000094; A61B 1/00042; A61B 1/0655; A61B 1/0005; A61B 1/0661;
(Continued)

(56) References Cited

U.S. PATENT DOCUMENTS

2015/0245002 A1    8/2015   Kuramoto
2016/0089010 A1*   3/2016   Aoyama .............. A61B 1/0005
                                                        348/70
(Continued)

FOREIGN PATENT DOCUMENTS

JP    2012-152246 A    8/2012
JP    2015-159957 A    9/2015
(Continued)

OTHER PUBLICATIONS

An Office Action; "Notice of Reasons for Refusal," mailed by the Japanese Patent Office on Mar. 8, 2022, which corresponds to Japanese Patent Application No. 2020-569410 and is related to U.S. Appl. No. 17/372,648 with English language translation.
(Continued)

*Primary Examiner* — Timothy J Neal
*Assistant Examiner* — James Edward Boice
(74) *Attorney, Agent, or Firm* — Studebaker & Brackett PC

(57) ABSTRACT

The endoscope system includes a light source unit, a light source controller, an image acquisition unit, a white balance unit, and a correction factor-calculating unit. The white balance unit multiplies a first image signal by a first gain factor, multiplies a second image signal by a second gain factor, and performs white balance processing using a corrected gain factor that is obtained through the correction of at least one of the first gain factor or the second gain factor.

16 Claims, 17 Drawing Sheets

(52) U.S. Cl.
CPC .......... *A61B 1/0655* (2022.02); *A61B 1/0661* (2013.01); *A61B 1/3137* (2013.01)

(58) Field of Classification Search
CPC ........ A61B 1/3137; A61B 1/06; G02B 23/24; G02B 23/26
USPC .......................................................... 600/160
See application file for complete search history.

(56) References Cited

U.S. PATENT DOCUMENTS

| | | | |
|---|---|---|---|
| 2017/0231502 | A1 | 8/2017 | Nagaoka |
| 2017/0290496 | A1* | 10/2017 | Fukuda .............. G02B 23/2453 |
| 2018/0376119 | A1 | 12/2018 | Iwane |

FOREIGN PATENT DOCUMENTS

| | | |
|---|---|---|
| JP | 2015-173737 A | 10/2015 |
| JP | 2017-113458 A | 6/2017 |
| JP | 2017-185258 A | 10/2017 |
| JP | 2017-202241 A | 11/2017 |
| JP | 2019-005096 A | 1/2019 |
| WO | 2016/080130 A1 | 5/2016 |

OTHER PUBLICATIONS

An Office Action mailed by China National Intellectual Property Administration on Oct. 8, 2022, which corresponds to Chinese Application No. 201980090845.5 and is related to U.S. Appl. No. 17/372,648; with English language translation.

International Search Report issued in PCT/JP2019/047008; mailed Feb. 10, 2020.

International Preliminary Report On Patentability and Written Opinion issued in PCT/JP2019/047008; issued Jul. 27, 2021.

* cited by examiner

FIG. 9
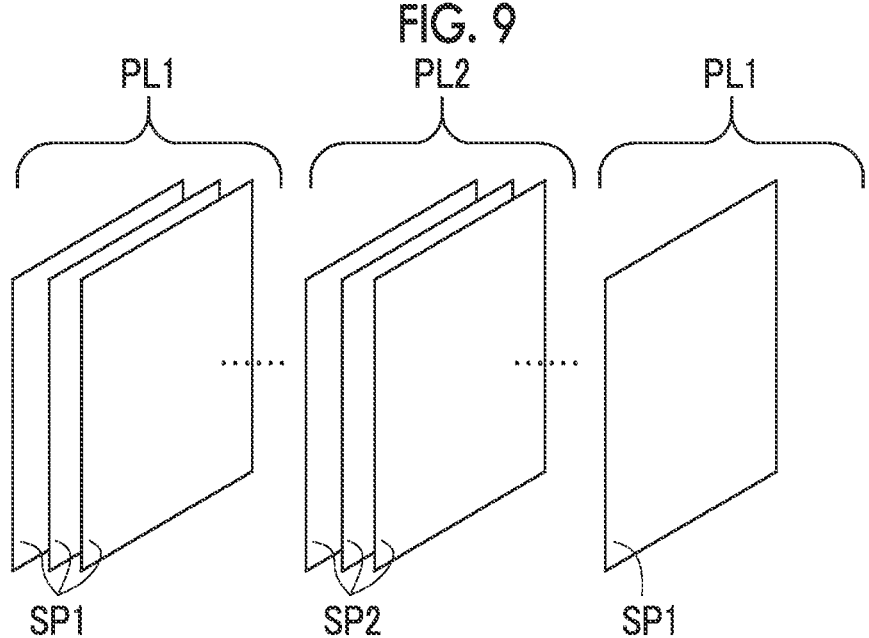
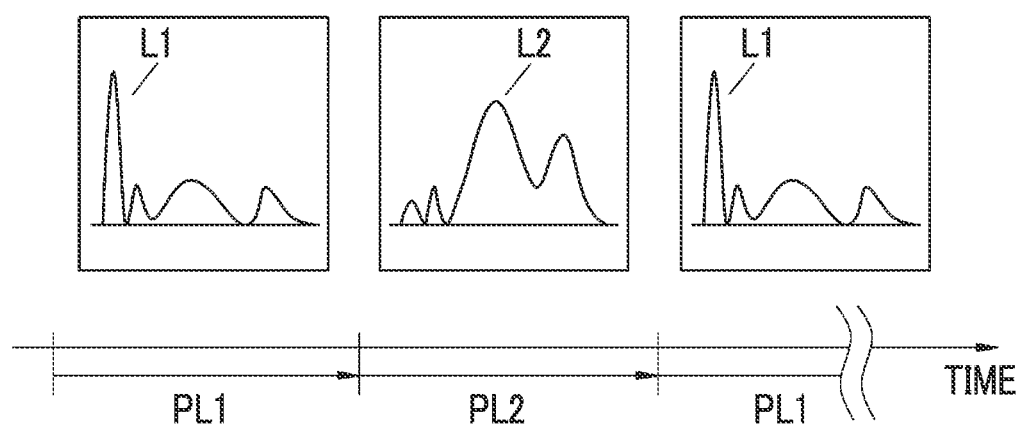
FIG. 10
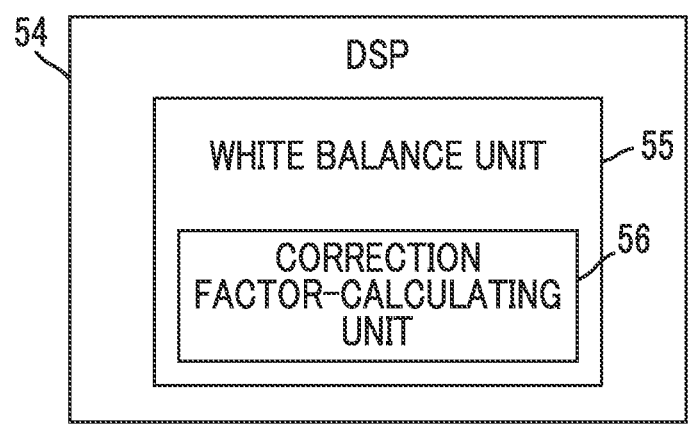

ENDOSCOPE SYSTEM

CROSS-REFERENCE TO RELATED APPLICATIONS

This application is a Continuation of PCT International Application No. PCT/JP2019/047008 filed on 2 Dec. 2019, which claims priority under 35 U.S.C § 119(a) to Japanese Patent Application No. 2019-014802 filed on 30 Jan. 2019. The above application is hereby expressly incorporated by reference, in its entirety, into the present application.

BACKGROUND OF THE INVENTION

1. Field of the Invention

The present invention relates to an endoscope system that switches and displays a plurality of kinds of images.

2. Description of the Related Art

In recent years, an endoscope system comprising a light source device, an endoscope, and a processor device has been widely used in a medical field. In the endoscope system, an object to be observed is irradiated with illumination light from an endoscope, and the image of the object to be observed is displayed on a monitor on the basis of RGB image signals that are obtained in a case where the image of the object to be observed, which is being illuminated with the illumination light, is picked up by an image pickup element of the endoscope.

In recent years, an object to be observed has been illuminated with a plurality of kinds of illumination light having wavelength ranges different from each other according to the purpose of diagnosis. For example, JP2015-173737A discloses that an object to be observed is alternately illuminated with two kinds of blue narrow-band light, that is, NB1 light having a peak wavelength of 422 nm and NB2 light having a peak wavelength in the range of 460 to 470 nm to acquire oxygen saturation in blood vessels included in the object to be observed. Further, WO2016/080130A (corresponding to US2017/231502A1) discloses that an object to be observed is illuminated with light having a peak in a B1 region (first B region: 390 nm to 440 nm) and light having a peak in a B2 region (second B region: 440 nm to 490 nm) and the image of the object to be observed is picked up by an image pickup element including B-pixels having sensitivity to both light of the B1 region and light of the B2 region to obtain image information about superficial blood vessels. Furthermore, JP2017-185258A discloses that desired tissue information about biological tissue is acquired in a more clear state suitable for diagnosis using violet light having a central wavelength of 405 nm, blue laser light having a central wavelength of 445 nm, and the excitation emission of light excited and emitted by blue laser light.

SUMMARY OF THE INVENTION

In recent years, a diagnosis focusing on biological information other than a background mucous membrane, for example, blood vessels having different depths, glandular structures having different depths or heights, or the like has been made in an endoscopic field. A plurality of kinds of information other than the background mucous membrane need to be displayed in such a diagnosis so that a user can grasp the information. A method including illuminating an object with various kinds of light, which have different invasion depths to biological tissue and a plurality of wavelengths, while automatically and periodically switching the various kinds of light and switching and displaying a plurality of images obtained through the illumination of the various kinds of light is considered as a method of displaying the plurality of kinds of information, respectively. For example, in order to obtain information about a surface layer, such as superficial blood vessels, and information about a deep layer, such as deep blood vessels, a user illuminates an object with short-wavelength light having an invasion depth to a surface layer and medium-wavelength light having an invasion depth to a deep layer while switching the short-wavelength light and the medium-wavelength light, and switches and displays a surface layer image obtained through the illumination of the short-wavelength light and a deep layer image obtained through the illumination of the medium-wavelength light. Since a difference between the surface layer image and the deep layer image is displayed in a case where such switching display is performed, different biological information can be separated and displayed. Accordingly, a user can grasp biological information different from the surface layer information and the deep layer information.

However, in a case where an object is illuminated with the short-wavelength light and the medium-wavelength light while the short-wavelength light and the medium-wavelength light are switched, the tint of the entire surface layer image and the tint of the entire deep layer image are different from each other in a case where the signal values of the surface layer image are significantly different from the signal values of the deep layer image. Accordingly, for example, in a case where an object is illuminated with the short-wavelength light and the medium-wavelength light while the short-wavelength light and the medium-wavelength light are automatically switched, images having different tints are automatically switched and displayed. For this reason, there is a concern that a screen may be uncomfortable to see. Further, there is a concern that the visibility of surface layer information and deep layer information on which a user focuses during a diagnosis may deteriorate.

Since a normal mucous membrane and an inflamed mucous membrane are made to have the same tone in a case where a tone is always made to match with a reference color as with auto white balance in order to prevent these, there is a concern that a correct diagnosis cannot be made. Further, in order to cope with this concern, a method including assuming a standard subject, such as a mucous membrane, in advance and performing white balance processing or the like on, for example, light having each wavelength using preset different gain factors so that tones and brightness are the same in images picked up using various kinds of light having a plurality of wavelengths is considered. However, even though a user copes with this concern in this way, spectral reflectivity is different from the spectral reflectivity of the standard subject depending on the change of a subject, such as a difference in a portion to be observed, an individual difference, the presence or absence of diseases, such as inflammation, or the presence or absence of the spraying of dye, and the brightness, tones, and the like of the respective images picked up using various kinds of light having a plurality of wavelengths are significantly different from each other. For this reason, there may be a problem that it is difficult to recognize a difference in target biological information.

An object of the invention is to provide an endoscope system that allows a user to easily recognize a difference between images while causing the brightness, tones, and the like of the respective images to match according to the change of a subject in a case where the subject is illuminated with a plurality of kinds of light while the plurality of kinds of light are switched and a plurality of images obtained through the illumination of the respective kinds of light are switched and displayed.

An endoscope system according to an aspect of the invention comprises a light source unit, a light source controller, an image acquisition unit, and a white balance unit. The light source unit emits first illumination light and second illumination light having an emission spectrum different from an emission spectrum of the first illumination light. The light source controller performs control to automatically switch and emit the first illumination light and the second illumination light and each of a light emission period in which the first illumination light is emitted and a light emission period in which the second illumination light is emitted is a light emission period of at least one or more frames. The image acquisition unit acquires a first image signal group including a first image signal obtained from image pickup of a subject illuminated with the first illumination light in the light emission period of the first illumination light and a second image signal group including a second image signal obtained from image pickup of the subject illuminated with the second illumination light in the light emission period of the second illumination light. The white balance unit multiplies the first image signal by a first gain factor and multiplies the second image signal by a second gain factor to perform white balance processing. The white balance unit performs the white balance processing using a corrected gain factor that is obtained through correction of at least one of the first gain factor or the second gain factor.

It is preferable that the white balance unit performs the white balance processing using the second gain factor fixed and not corrected.

It is preferable that the first image signal or the second image signal includes a blue color signal, a red color signal, and a green color signal, and a signal value of the first image signal or a signal value of the second image signal consists of a blue color signal value, a red color signal value, and a green color signal value.

It is preferable that the white balance unit determines the first gain factor or the second gain factor for each of the blue color signal value, the red color signal value, and the green color signal value.

It is preferable that, in a case where the first gain factor is to be corrected, the first gain factor of an acquisition period $P_N$ (N is an integer) used for the first image signal included in the first image signal group of the acquisition period $P_N$ is a corrected first gain factor obtained through correction of the first gain factor of an acquisition period $P_{N-2}$ immediately before the acquisition period $P_N$ used for the first image signal of the acquisition period $P_{N-2}$.

It is preferable that, in a case where the first gain factor is to be corrected, each of at least some of the first gain factors of a plurality of acquisition periods $P_{N-K}$ (K is an even number of 2 or more) before an acquisition period $P_N$ used for the first image signals included in the first image signal groups of the plurality of acquisition periods $P_{N-K}$ is the corrected gain factor having been subjected to correction, the first gain factor of the acquisition period $P_N$ used for the first image signal included in the first image signal group of the acquisition period $P_N$ is a value of a sum of respective products of the first gain factors of the plurality of acquisition periods $P_{N-K}$ and weighting factors, and the weighting factor is larger as an acquisition period is closer to the acquisition period $P_N$.

It is preferable that the first gain factors of the plurality of acquisition periods $P_{N-K}$ are used for the white balance processing in the respective acquisition periods $P_{N-K}$.

It is preferable that a correction factor used to correct at least one of the first gain factor or the second gain factor is used for the correction of the first gain factor or the second gain factor, and the correction factor is calculated using a first calculation value obtained from calculation based on the first image signal group and a second calculation value obtained from calculation based on the second image signal group.

It is preferable that the first calculation value is obtained from arithmetic averaging of respective first image signal value averages obtained from averaging of signal values of the first image signals in the first image signals included in the first image signal group and the second calculation value is obtained from arithmetic averaging of respective second image signal value averages obtained from averaging of signal values of the second image signals in the second image signals included in the second image signal group.

It is preferable that the endoscope system further comprises a detection unit detecting an image signal of a blood vessel or a lesion portion in the first image signals or the second image signals and regards the detected image signal as an abnormal image signal, and the first image signal value average or the second image signal value average is obtained using the signal values of the first image signals or the signal values of the second image signals except for the abnormal image signal, respectively.

It is preferable that the endoscope system further comprises a detection unit detecting an image signal of an abnormal pixel portion in the first image signals or the second image signals and regards the detected abnormal pixel portion as an abnormal image signal, and the first image signal value average or the second image signal value average is obtained using the signal values of the first image signals or the signal values of the second image signals except for the abnormal image signal, respectively.

It is preferable that the correction factor is a ratio between the first and second calculation values.

It is preferable that the first gain factor of the acquisition period $P_N$ is a value of a product of the first gain factor, which is used for the first image signal included in the first image signal group of the acquisition period $P_{N-2}$, and a value of a ratio between the first calculation value of the acquisition period $P_{N-2}$ and the second calculation value of the acquisition period $P_{N-1}$.

It is preferable that the first gain factor of the acquisition period $P_N$ is not corrected in a case where a difference between the first gain factor of the acquisition period $P_N$ and the first gain factor used for the first image signal included in the first image signal group of the acquisition period $P_{N-2}$ is equal to or smaller than a preset threshold value.

It is preferable that the first gain factor of the acquisition period $P_N$ is not corrected in a case where a difference between the first gain factor of the acquisition period $P_N$ and the first gain factor used for the first image signal included in the first image signal group of the acquisition period $P_{N-2}$ is equal to or larger than a preset threshold value.

It is preferable that the first illumination light includes violet light, green light, and red light and the second illumination light includes blue light, green light, and red light and the light source controller controls an amount of each color light, which is included in the first illumination light and the second illumination light, to be emitted on a basis of the first gain factor or the second gain factor.

It is preferable that the light source controller increases the amount of light to be emitted up to a preset minimum amount of light to be emitted in a case where the amount of light to be emitted controlled on the basis of the first gain factor or the second gain factor is equal to or smaller than a specific threshold value.

It is preferable that the image processing unit generates a first observation image for display by the first image signal and generates a second observation image for display by the second image signal, and a superficial blood vessel is emphasized in the first observation image for display and a medium-deep blood vessel present at a position deeper than the superficial blood vessel is emphasized in the second observation image for display.

According to the invention, it is possible to provide an endoscope system that allows a user to easily recognize a difference between images while causing the brightness, tones, and the like of the respective images to match according to the change of a subject in a case where the subject is illuminated with a plurality of kinds of light while the plurality of kinds of light are switched and a plurality of images obtained through the illumination of the respective kinds of light are switched and displayed.

BRIEF DESCRIPTION OF THE DRAWINGS

FIG. 9 is a diagram illustrating the acquisition of a first image signal group and a second image signal group in time series.

FIG. 10 is a block diagram showing the functions of a DSP.

DESCRIPTION OF THE PREFERRED EMBODIMENTS

Figure 1:
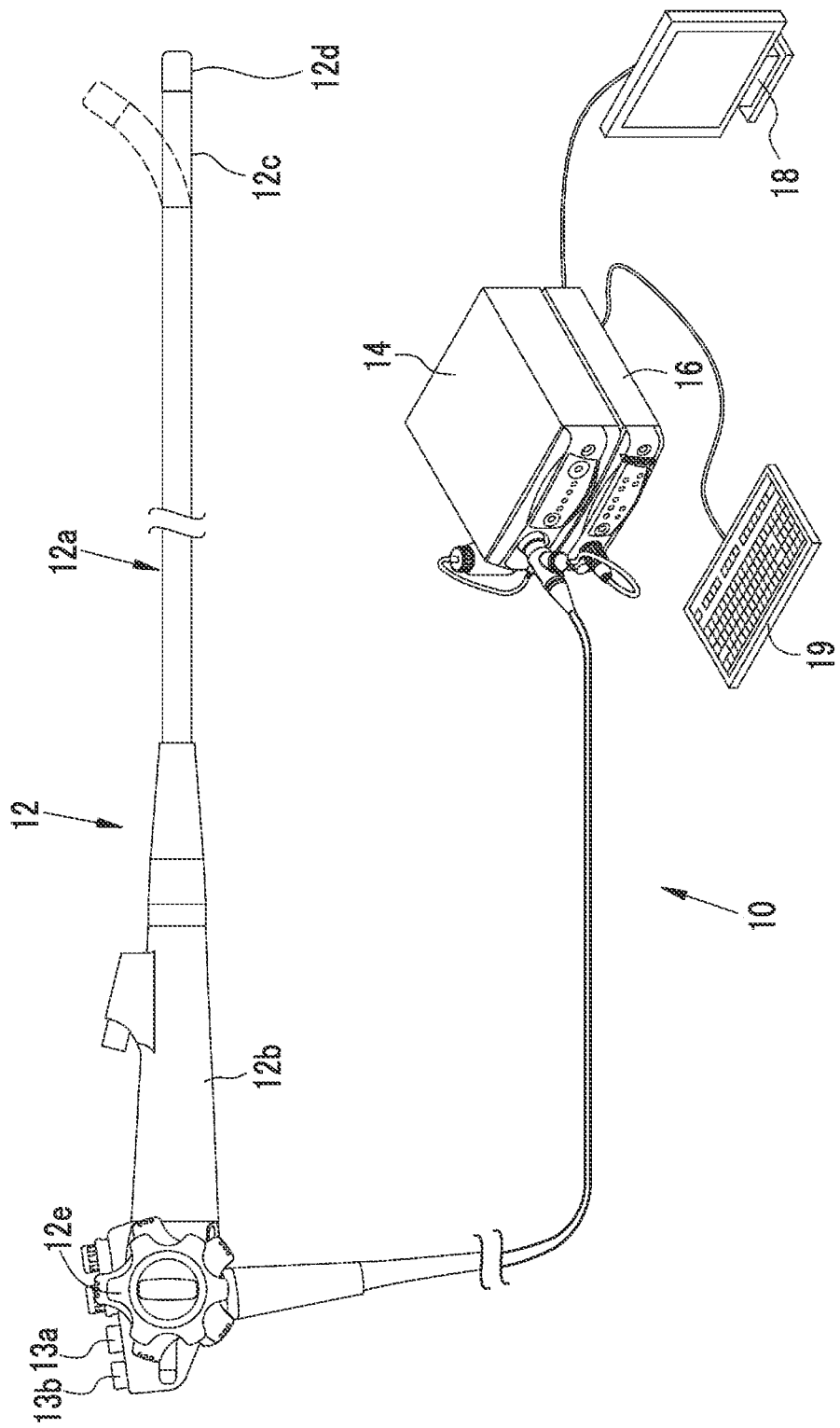
FIG. 1 is a diagram showing the appearance of an endoscope system.

As shown in FIG. 1, an endoscope system 10 according to an embodiment includes an endoscope 12, a light source device 14, a processor device 16, a monitor 18 (display unit), and a user interface 19. The endoscope 12 is optically connected to the light source device 14, and is electrically connected to the processor device 16. The endoscope 12 includes an insertion part 12a that is to be inserted into an object to be examined, an operation part 12b that is provided at the proximal end portion of the insertion part 12a, and a bendable part 12c and a distal end part 12d that are provided on the distal end side of the insertion part 12a. In a case where angle knobs 12e of the operation part 12b are operated, the bendable part 12c is operated to be bent. As the bendable part 12c is operated to be bent, the distal end part 12d is made to face in a desired direction. The user interface 19 includes a mouse and the like in addition to a keyboard shown in FIG. 1.

Further, the operation part 12b is provided with a mode changeover SW 13a and a static image-acquisition instruction unit 13b in addition to the angle knobs 12e. The mode changeover SW 13a is used for an operation for switching a normal observation mode, a first special observation mode, a second special observation mode, and a multi-observation mode. The normal observation mode is a mode where a normal image is displayed on the monitor 18. The first special observation mode is a mode where a first special observation image in which surface layer information, such as superficial blood vessels, are emphasized is displayed on the monitor 18. The second special observation mode is a mode where a second special observation image in which deep layer information, such as deep blood vessels, are emphasized is displayed on the monitor 18. The multi-observation mode is a mode where the first special observation image (hereinafter, referred to as a first image) and the second special observation image (hereinafter, referred to as a second image) are automatically switched and displayed on the monitor 18. In order to switch a mode, a foot switch or the like may be used other than the mode changeover SW 13a.

The processor device 16 is electrically connected to the monitor 18 and the user interface 19. The monitor 18 outputs and displays image information and the like. The user interface 19 functions as a user interface (UI) that receives an input operation, such as function settings. An external recording unit (not shown), which records image information and the like, may be connected to the processor device 16.

Figure 2:
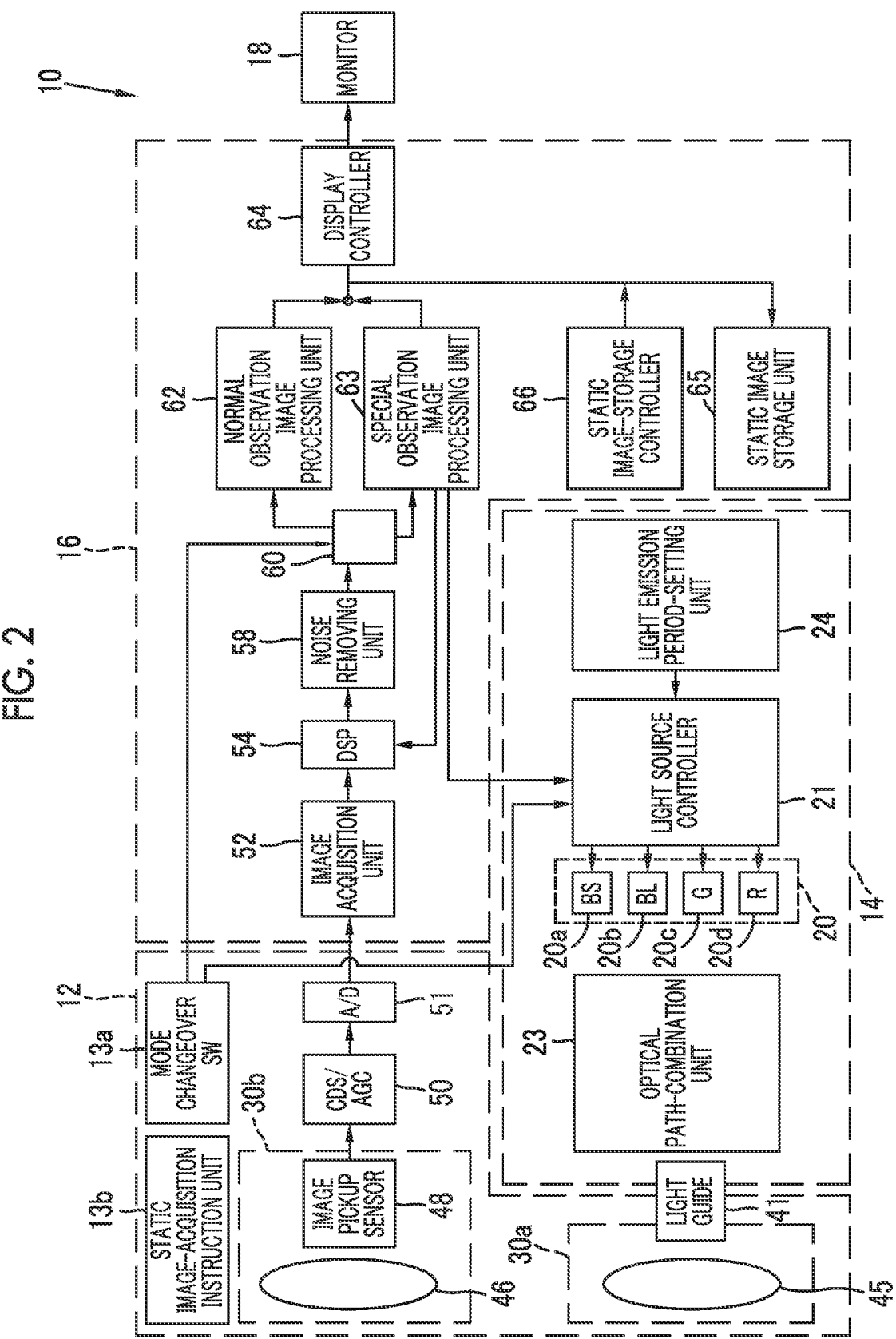
FIG. 2 is a block diagram showing the functions of the endoscope system.

As shown in FIG. 2, the light source device 14 includes a light source unit 20, a light source controller 21, an optical path-combination unit 23, and a light emission period-setting unit 24. The light source unit 20 includes a violet light emitting diode (V-LED) 20a, a blue light emitting diode (B-LED) 20b, a green light emitting diode (G-LED) 20c, and a red light emitting diode (R-LED) 20d. The light source controller 21 controls the drive of the LEDs 20a to 20d. The optical path-combination unit 23 combines the optical paths of four kinds of color light that are emitted from the four color LEDs 20a to 20d. The inside of an object to be examined is irradiated with the pieces of light, which are combined by the optical path-combination unit 23, through a light guide 41 inserted into the insertion part 12a and an illumination lens 45. A laser diode (LD) may be used instead of the LED. The light emission period-setting unit 24 sets the light emission periods of a plurality of pieces of illumination light.

Figure 3:
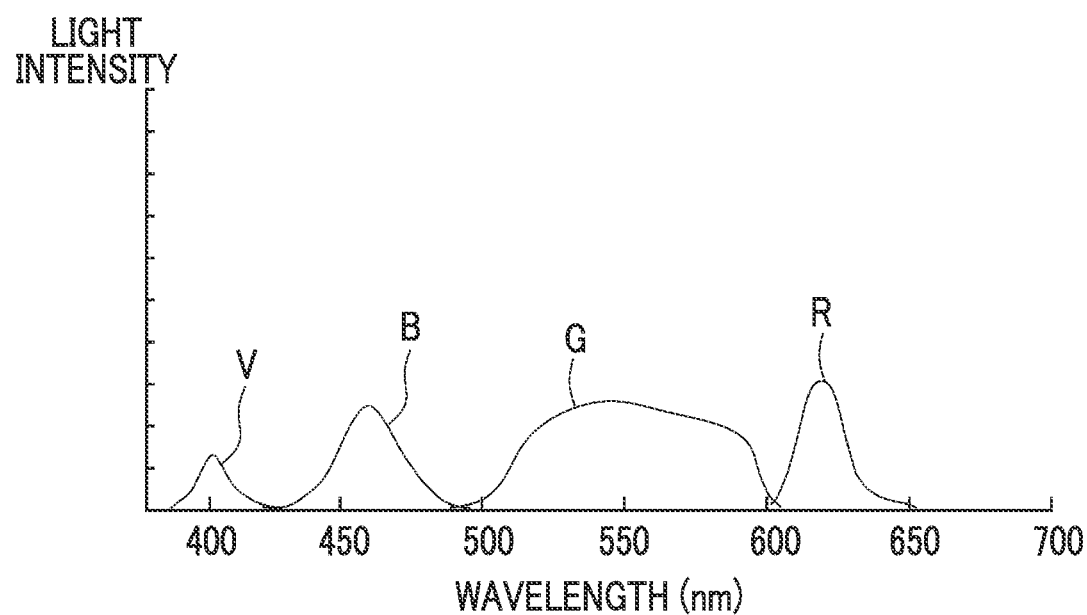
FIG. 3 is a graph showing the emission spectra of violet light V, blue light B, green light G, and red light R.

As shown in FIG. 3, the V-LED 20a generates violet light V of which the central wavelength is in the range of 405±10 nm and the wavelength range is in the range of 380 to 420 nm. The B-LED 20b generates blue light B of which the central wavelength is in the range of 460±10 nm and the wavelength range is in the range of 420 to 500 nm. The G-LED 20c generates green light G of which the wavelength range is in the range of 480 to 600 nm. The R-LED 20d generates red light R of which the central wavelength is in the range of 620 to 630 nm and the wavelength range is in the range of 600 to 650 nm.

The light source controller 21 controls the V-LED 20a, the B-LED 20b, the G-LED 20c, and the R-LED 20d. Further, the light source controller 21 controls the respective LEDs 20a to 20d so that normal light of which the light intensity ratios of violet light V, blue light B, green light G, and red light R are Vc:Bc:Gc:Rc is emitted in the normal observation mode.

Figure 4:
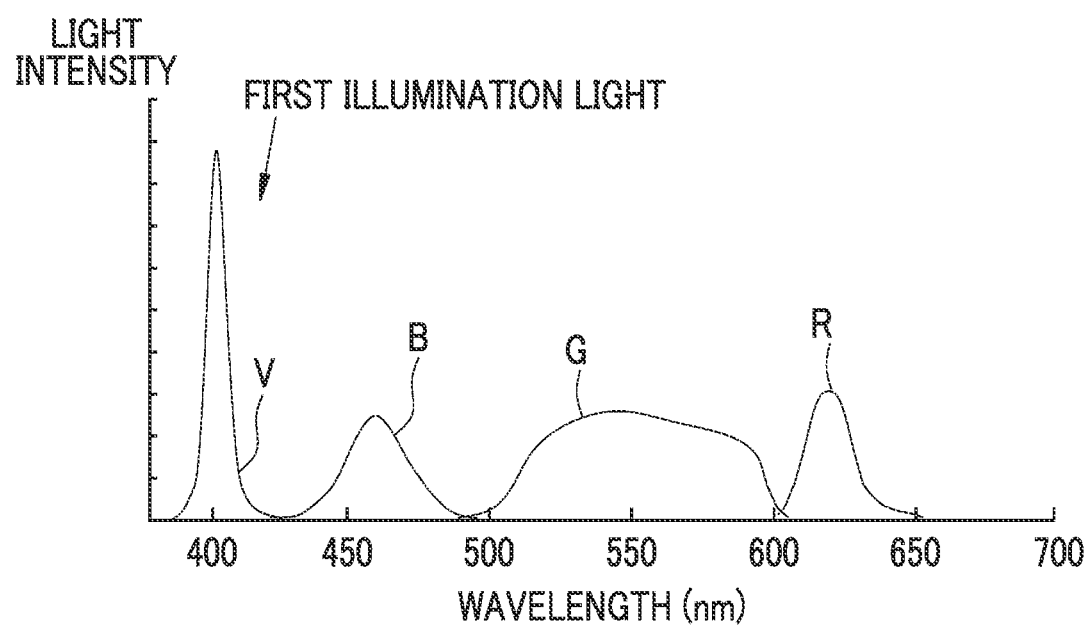
FIG. 4 is a graph showing the emission spectrum of first illumination light that includes violet light V, blue light B, green light G, and red light R.

Furthermore, the light source controller 21 controls the respective LEDs 20a to 20d so that first illumination light of which the light intensity ratios of violet light V, blue light B, green light G, and red light R are Vs1:Bs1:Gs1:Rs1 is emitted in the first special observation mode. The light intensity ratios Vs1:Bs1:Gs1:Rs1 correspond to the light amount condition of the first illumination light. It is preferable that the first illumination light emphasizes superficial blood vessels. For this purpose, it is preferable that the light intensity of violet light V of the first illumination light is set to be higher than the light intensity of the blue light B thereof. For example, as shown in FIG. 4, a ratio of the light intensity Vs1 of violet light V to the light intensity Bs1 of blue light B is set to "4:1".

In this specification, the light intensity ratios include a case where the ratio of at least one semiconductor light source is 0 (zero). Accordingly, the light intensity ratios include a case where any one or two or more of the respective semiconductor light sources are not turned on. For example, even though only one semiconductor light source is turned on and the other three semiconductor light sources are not turned on as in a case where the light intensity ratios of violet light V, blue light B, green light G, and red light R are 1:0:0:0, it is regarded that the light source unit 20 has light intensity ratios.

Figure 5:
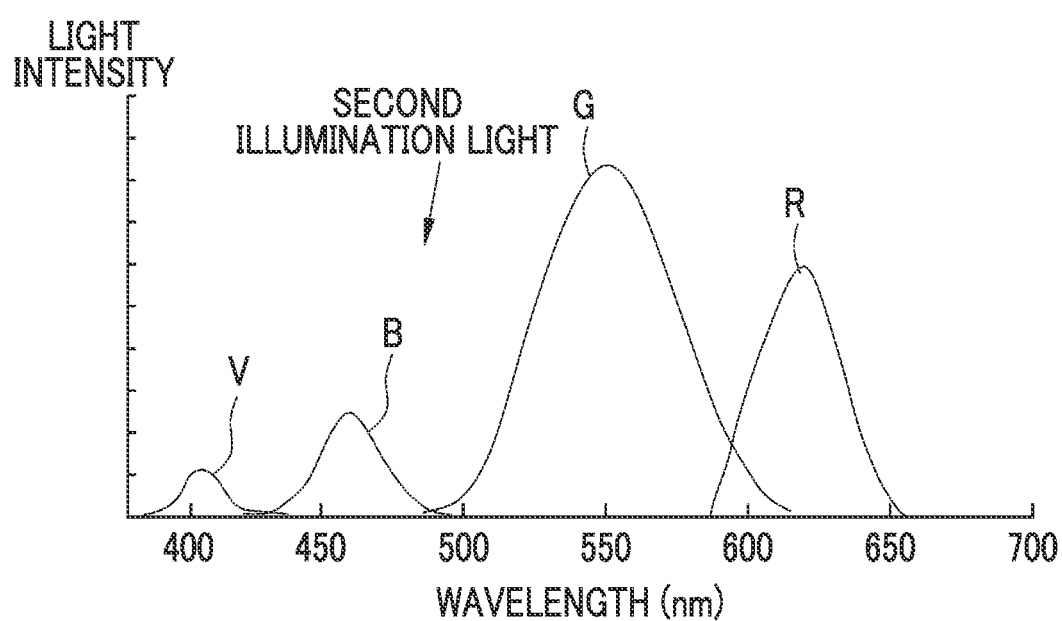
FIG. 5 is a graph showing the emission spectrum of second illumination light that includes violet light V, blue light B, green light G, and red light R.

Further, the light source controller 21 controls the respective LEDs 20a to 20d so that second illumination light of which the light intensity ratios of violet light V, blue light B, green light G, and red light R are Vs2:Bs2:Gs2:Rs2 is emitted in the second special observation mode. The light intensity ratios Vs2:Bs2:Gs2:Rs2 correspond to the light amount condition of the second illumination light. It is preferable that the second illumination light emphasizes deep blood vessels. For this purpose, it is preferable that the light intensity of blue light B of the second illumination light is set to be higher than the light intensity of the violet light V thereof. For example, as shown in FIG. 5, a ratio of the light intensity Vs2 of violet light V to the light intensity Bs2 of blue light B is set to "1:3".

In a case where a mode is set to the multi-observation mode, the light source controller 21 performs control to emit the first illumination light and the second illumination light for light emission periods of a first period and a second period, respectively, and to automatically switch and emit the first illumination light and the second illumination light. Each of the first and second periods has a light emission period of at least one or more frames.

Figure 6:
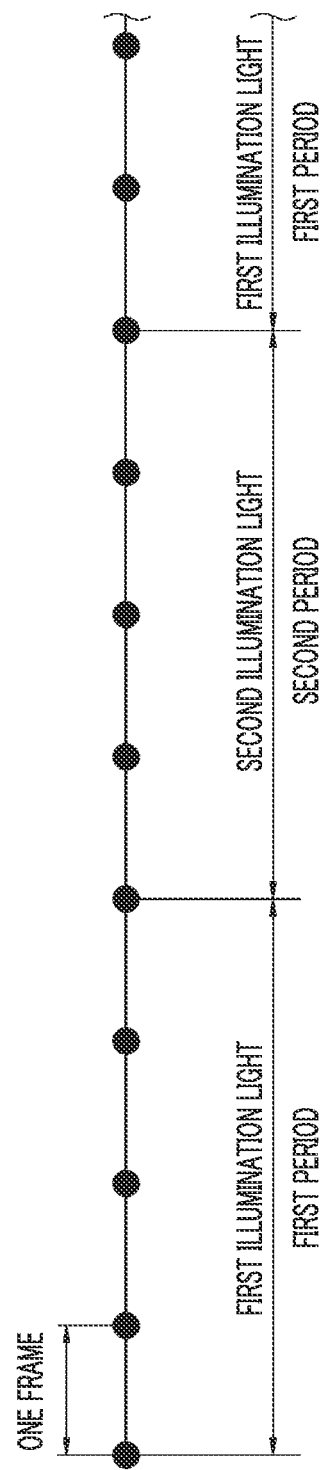
FIG. 6 is a diagram illustrating the light emission period of the first illumination light and the light emission period of the second illumination light.

More specifically, in a case where the light source controller 21 sets the first period to four frames and sets the second period to four frames, the second illumination light continues to be emitted for four frames after the first illumination light continues to be emitted for four frames as shown in, for example, FIG. 6. Then, this light emission pattern is repeated.

"Frame" means a unit used to control an image pickup sensor 48 (see FIG. 2) that picks up the image of an object to be observed. For example, "one frame" means a period including at least an exposure period where the image pickup sensor 48 is exposed to light emitted from an object to be observed and a read-out period where image signals are read out. In this embodiment, the first period or the second period is determined so as to correspond to "frame" that is a unit of image pickup.

Figure 7:
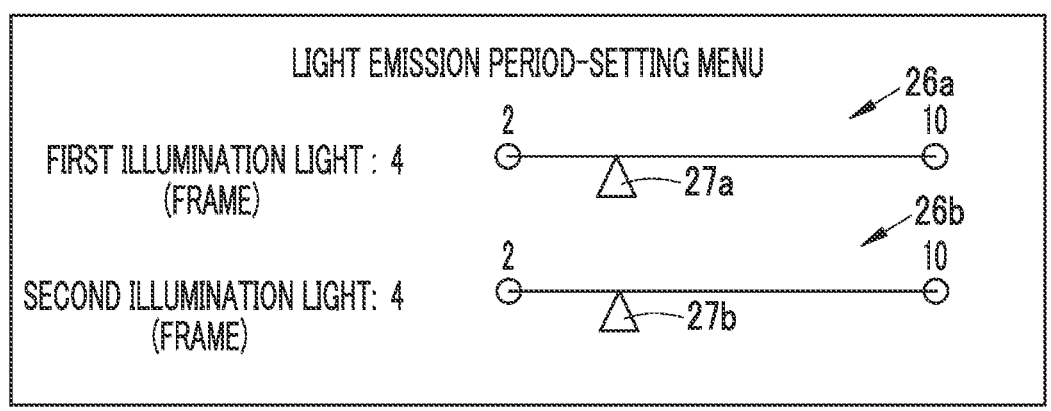
FIG. 7 is a diagram illustrating a light emission period-setting menu.

The first period that is the light emission period of the first illumination light and the second period that is the light emission period of the second illumination light can be appropriately changed by the light emission period-setting unit 24 that is connected to the light source controller 21. In a case where an operation for changing a light emission period is received by the operation of the user interface 19, the light emission period-setting unit 24 displays a light emission period-setting menu shown in FIG. 7 on the monitor 18. The first period can be changed between, for example, two frames and ten frames. Each light emission period is assigned to a slide bar 26a.

In a case where the first period is to be changed, a user operates the user interface 19 to position a slider 27a at a position on the slide bar 26a that represents a light emission period to which the user wants to change a light emission period. Accordingly, the first period is changed. Even in the case of the second period, a user operates the user interface 19 to position a slider 27b at a position on a slide bar 26b that represents a light emission period to which the user wants to change a light emission period. Accordingly, the second period is changed. A light emission period in the range of, for example, two frames to ten frames is assigned to even the slide bar 26b.

As shown in FIG. 2, the light guide 41 is built in the endoscope 12 and a universal cord (a cord connecting the endoscope 12 to the light source device 14 and the processor device 16), and transmits the pieces of light, which are combined by the optical path-combination unit 23, to the distal end part 12d of the endoscope 12. A multimode fiber can be used as the light guide 41. For example, a thin fiber cable of which a total diameter of a core diameter of 105 μm, a cladding diameter of 125 μm, and a protective layer forming a covering is in the range of tri 0.3 to 0.5 mm can be used.

The distal end part 12d of the endoscope 12 is provided with an illumination optical system 30a and an image pickup optical system 30b. The illumination optical system 30a includes an illumination lens 45, and an object to be observed is irradiated with light transmitted from the light guide 41 through the illumination lens 45. The image pickup optical system 30b includes an objective lens 46 and an image pickup sensor 48. Light reflected from the object to be observed is incident on the image pickup sensor 48 through the objective lens 46. Accordingly, the reflected image of the object to be observed is formed on the image pickup sensor 48.

The image pickup sensor 48 is a color image pickup sensor, and picks up the reflected image of an object to be examined and outputs image signals. It is preferable that the image pickup sensor 48 is a charge coupled device (CCD) image pickup sensor, a complementary metal-oxide semi-conductor (CMOS) image pickup sensor, or the like. The image pickup sensor 48 used in the embodiment of the present invention is a color image pickup sensor used to obtain RGB image signals corresponding to three colors of R (red), G (green), and B (blue), that is, a so-called RGB image pickup sensor that comprises R-pixels provided with R-filters, G-pixels provided with G-filters, and B-pixels provided with B-filters.

Figure 8:
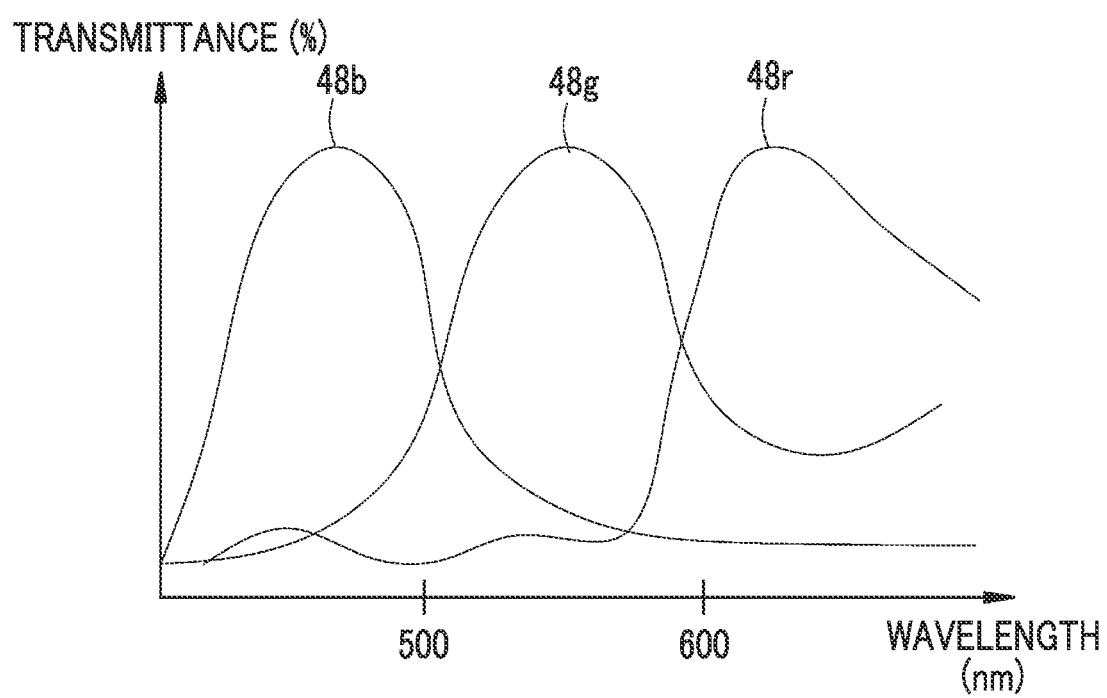
FIG. 8 shows the spectral transmittance of a B-filter, a G-filter, and an R-filter provided in an image pickup sensor.

As shown in FIG. 8, the B-filter 48b transmits light of a violet-light wavelength range, light of a blue-light wavelength range, and short-wavelength light of light of a green-light wavelength range. The G-filter 48g transmits light of a green-light wavelength range, long-wavelength light of light of a blue-light wavelength range, and short-wavelength light of light of a red-light wavelength range. The R-filter 48r transmits light of a red-light wavelength range and long-wavelength light of light of a green-light wavelength range. Accordingly, in the image pickup sensor 48, the B-pixel has sensitivity to violet light V and blue light B, the G-pixel has sensitivity to blue light B, green light G, and red light R, and the R-pixel has sensitivity to green light G and red light R.

The image pickup sensor 48 may be a so-called complementary color image pickup sensor, which comprises complementary color filters corresponding to C (cyan), M (magenta), Y (yellow), and G (green), instead of an RGB color image pickup sensor. In a case where a complementary color image pickup sensor is used, image signals corresponding to four colors of C, M, Y, and G are output. Accordingly, the image signals corresponding to four colors of C, M, Y, and G need to be converted into image signals corresponding to three colors of R, G, and B by complementary color-primary color conversion. Further, the image pickup sensor 48 may be a monochrome image pickup sensor that includes no color filter. In this case, since the light source controller 21 causes blue light B, green light G, and red light R to be emitted in a time-sharing manner, demosaicing needs to be added to processing for image pickup signals.

As shown in FIG. 2, the image signals output from the image pickup sensor 48 are transmitted to a CDS/AGC circuit 50. The CDS/AGC circuit 50 performs correlated double sampling (CDS) or auto gain control (AGC) on the image signals that are analog signals. The image signals, which have been transmitted through the CDS/AGC circuit 50, are converted into digital image signals by an analog/digital converter (A/D converter) 51. The digital image signals, which have been subjected to A/D conversion, are input to the processor device 16.

The processor device 16 comprises an image acquisition unit 52, a digital signal processor (DSP) 54, a noise removing unit 58, a signal switching unit 60, a normal observation image processing unit 62, a special observation image processing unit 63, a display controller 64, a static image storage unit 65, and a static image-storage controller 66.

The image acquisition unit 52 acquires an observation image that is obtained in a case where the image of the object to be observed is picked up in the endoscope 12. Specifically, digital color image signals obtained from the endoscope 12 are input to the image acquisition unit 52 as an observation image. The color image signals are formed of red color signals output from the R-pixels of the image pickup sensor 48, green color signals output from the G-pixels of the image pickup sensor 48, and blue color signals output from the B-pixels of the image pickup sensor 48.

As shown in FIG. 9, the image acquisition unit 52 acquires a first image signal group in the first period PL1. The first image signal group includes a plurality of first image signals SP1 that are obtained in the first period PL1 from the image pickup of a subject illuminated with the first illumination light L1. Further, the image acquisition unit 52 acquires a second image signal group in the second period PL2. The second image signal group includes a plurality of second image signals SP2 that are obtained in the second period PL2 from the image pickup of the subject illuminated with the second illumination light L2. In a case where a mode is set to the multi-observation mode in this embodiment, the light source controller 21 performs control to emit the first illumination light L1 and the second illumination light L2 for the light emission periods of the first period PL1 and the second period PL2, respectively, and to automatically switch and emit the first illumination light L1 and the second illumination light L2. Accordingly, the image acquisition unit 52 periodically acquires images in the order of the first image signal group and the second image signal group over time.

Since each of the first period PL1 and the second period PL2 has a light emission period of at least one or more frames, the first image signal group and the second image signal group include at least one or more first image signals SP1 and at least one or more second image signals SP2, respectively. In this embodiment, each of the first period PL1 and the second period PL2 is a light emission period of four frames. Accordingly, the first image signal group including four first image signals SP1 is acquired in the first period PL1 and the second image signal group including four second image signals SP2 is acquired in the second period PL2.

The DSP 54 performs various kinds of signal processing, such as defect correction processing, offset processing, white balance processing, linear matrix processing, gamma conversion processing, and demosaicing processing, on the received image signals. Further, the DSP 54 comprises a white balance unit 55 as shown in FIG. 10. Furthermore, the white balance unit 55 comprises a correction factor-calculating unit 56.

Signals of defective pixels of the image pickup sensor 48 are corrected in the defect correction processing. Dark current components are removed from the image signals having been subjected to the defect correction processing in the offset processing, so that an accurate zero level is set. The white balance unit 55 multiplies the first image signals by a first gain factor and multiplies the second image signals by a second gain factor to perform white balance processing. The first gain factor means a gain factor to be multiplied by the first image signals, and the second gain factor means a gain factor to be multiplied by the second image signals. The image signals having been subjected to the offset processing are multiplied by a gain in the white balance processing, so that signal levels are adjusted. The correction factor-calculating unit 56 calculates a correction factor that is used to correct at least one of the first gain factor or the second gain factor. Linear matrix processing for improving color reproducibility is performed on the image signals having been subjected to the white balance processing. After that, brightness or a saturation is adjusted by the gamma conversion processing. The demosaicing processing (also referred to as equalization processing or demosaicing) is performed on the image signals having been subjected to the linear matrix processing, so that signals of colors deficient in each pixel are generated by interpolation. All the pixels are made to have the signals of the respective colors by this demosaicing processing.

The noise removing unit 58 performs noise removal processing (for example, a moving-average method, median filtering, or the like) on the image signals, which have been subjected to gamma correction and the like by the DSP 54, to remove noise from the image signals. The image signals from which noise has been removed are transmitted to the signal switching unit 60.

Figure 11:
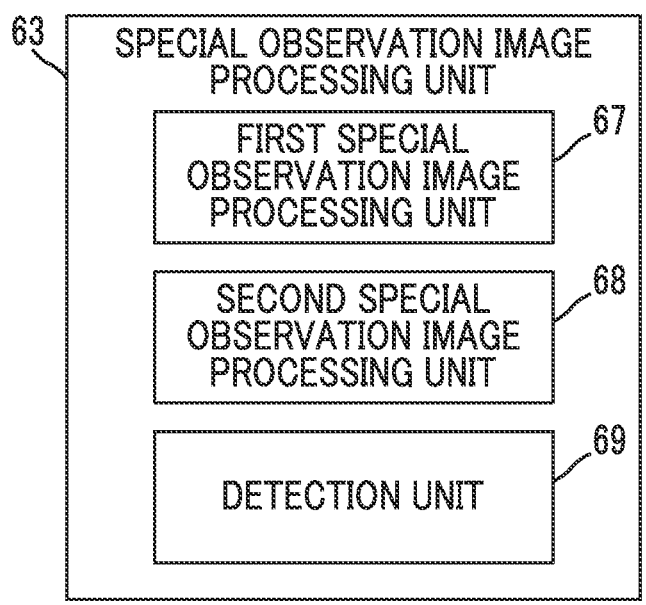
FIG. 11 is a block diagram showing the functions of a special image processing unit.

In a case where a mode is set to the normal observation mode by the mode changeover SW 13a, the signal switching unit 60 transmits image signals for normal light, which are obtained through the illumination of normal light and image pickup, to the normal observation image processing unit 62. As shown in FIG. 11, the special observation image processing unit 63 includes a first special observation image processing unit 67, a second special observation image processing unit 68, and a detection unit 69. Further, in a case where a mode is set to the first special observation mode, the signal switching unit 60 transmits first image signals, which are obtained through the illumination of the first illumination light and image pickup, to the first special observation image processing unit 67. The first image signals include first red color signals that are output from the R-pixels of the image pickup sensor, first green color signals that are output from the G-pixels of the image pickup sensor 48, and first blue color signals that are output from the B-pixels of the image pickup sensor 48. Furthermore, in a case where a mode is set to the second special observation mode, the signal switching unit 60 transmits second image signals, which are obtained through the illumination of the second illumination light and image pickup, to the second special observation image processing unit 63. The second image signals include second red color signals that are output from the R-pixels of the image pickup sensor, second green color signals that are output from the G-pixels of the image pickup sensor 48, and second blue color signals that are output from the B-pixels of the image pickup sensor 48. Moreover, in a case where a mode is set to the multi-observation mode, first image signals obtained through the illumination of the first illumination light and image pickup are transmitted to the first special observation image processing unit 67 and second image signals obtained through the illumination of the second illumination light and image pickup are transmitted to the second special observation image processing unit 63.

The normal observation image processing unit 62 performs image processing for a normal image on the RGB image signals that are obtained in the normal observation mode. The image processing for a normal image includes structure emphasis processing for a normal image and the like. The normal observation image processing unit 62 includes parameters for a normal image, which are to be multiplied by the RGB image signals, to perform the image processing for a normal image. The RGB image signals having been subjected to the image processing for a normal image are input to the display controller 64 from the normal observation image processing unit 62 as a normal image.

The first special observation image processing unit 67 generates a first image having been subjected to image processing, such as saturation emphasis processing, hue emphasis processing, and structure emphasis processing, on the basis of the first image signals. In the first image, many superficial blood vessels are included and the color of the background mucous membrane is also accurately reproduced. The first special observation image processing unit 67 includes parameters for a first image, which are to be multiplied by the first image signals, to perform the image processing for a first image. The first special observation image processing unit 67 does not perform superficial blood vessel emphasis processing for emphasizing superficial blood vessels, but may perform the superficial blood vessel emphasis processing depending on the situation of a processing load.

Figure 12:
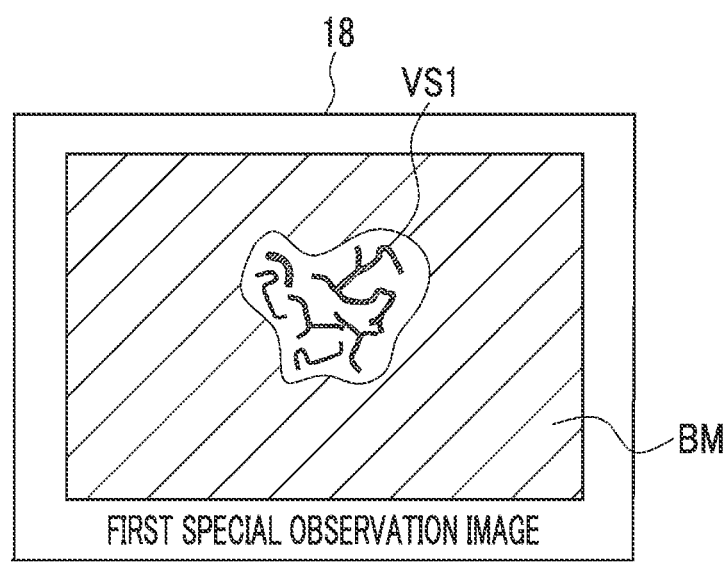
FIG. 12 is an image diagram showing a first special observation image (first image).
Figure 13:
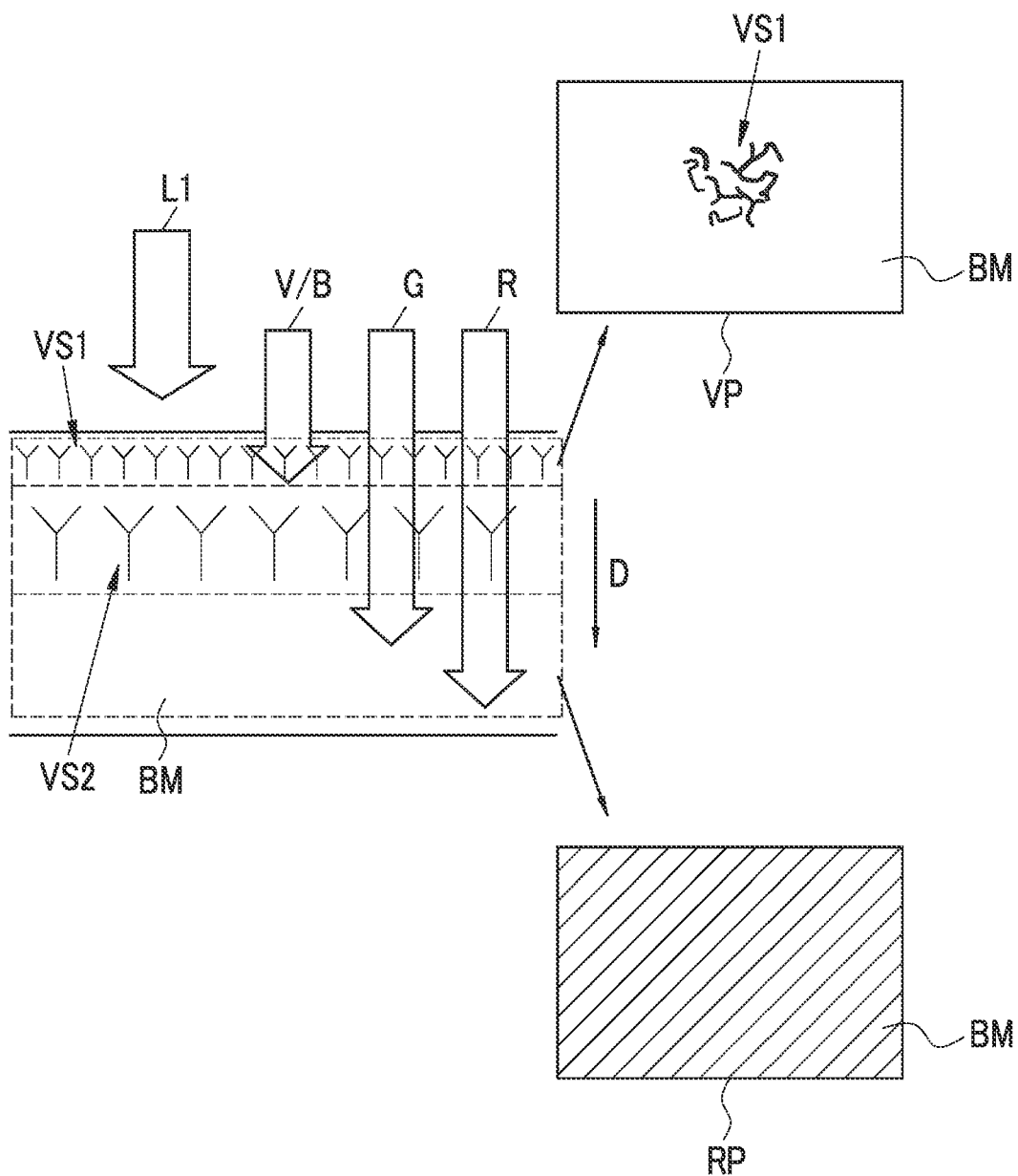
FIG. 13 is a diagram illustrating a violet-blue light image and a green-red light image that are obtained in a case where a subject is illuminated with the first illumination light.

An image in which a background mucous membrane BM and superficial blood vessels VS1 of an object to be observed are shown as shown in FIG. 12 is displayed by the first image. The first image is obtained on the basis of the first illumination light that includes violet light, blue light, green light, and red light. In a case where the object to be observed is illuminated with the first illumination light L1, violet light V and blue light B of the first illumination light L1 reach a surface layer where the superficial blood vessels VS1 are distributed as shown in FIG. 13. In FIG. 13, the object to be observed is illuminated with the first illumination light L1 from the upper side of the plane of paper and the lower side of the plane of paper corresponds to a depth direction D of the object to be observed. Since the light intensity of violet light V is higher than the light intensity of each of blue light B, green light G, and red light R in the first illumination light, the image of the superficial blood vessels VS1 included in a violet light image VP obtained on the basis of the reflected light of violet light V is emphasized. Here, since the light intensity of violet light V is higher than the light intensity of each of blue light B, green light G, and red light R, a violet light image VP is obtained. Further, red light R of the first illumination light L1 reaches the background mucous membrane BM that is distributed at a position deeper than the superficial blood vessels VS1 and deep blood vessels VS2 (blood vessels present at positions deeper than the superficial blood vessels VS1). Accordingly, the image of the background mucous membrane BM is included in a red light image RP that is obtained on the basis of the reflected light of red light R. Since the first image is an image in which the violet light image VP and the red light image RP are combined with each other as described above, the images of the background mucous membrane BM and the superficial blood vessels VS1 are displayed.

The second special observation image processing unit 68 generates a second image having been subjected to image processing, such as saturation emphasis processing, hue emphasis processing, and structure emphasis processing, on the basis of the second image signals. In the second image, many deep blood vessels are included and the color of the background mucous membrane is also accurately reproduced. The second special observation image processing unit 68 includes parameters for a second image, which are to be multiplied by the second image signals, to perform the image processing for a second image. The second special observation image processing unit 68 does not perform deep blood vessel emphasis processing for emphasizing deep blood vessels, but may perform the deep blood vessel emphasis processing depending on the situation of a processing load.

Figure 14:
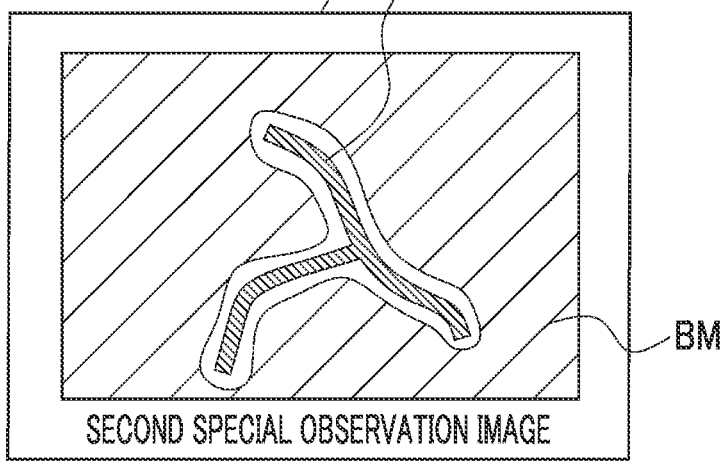
FIG. 14 is an image diagram showing a second special observation image (second image).
Figure 15:
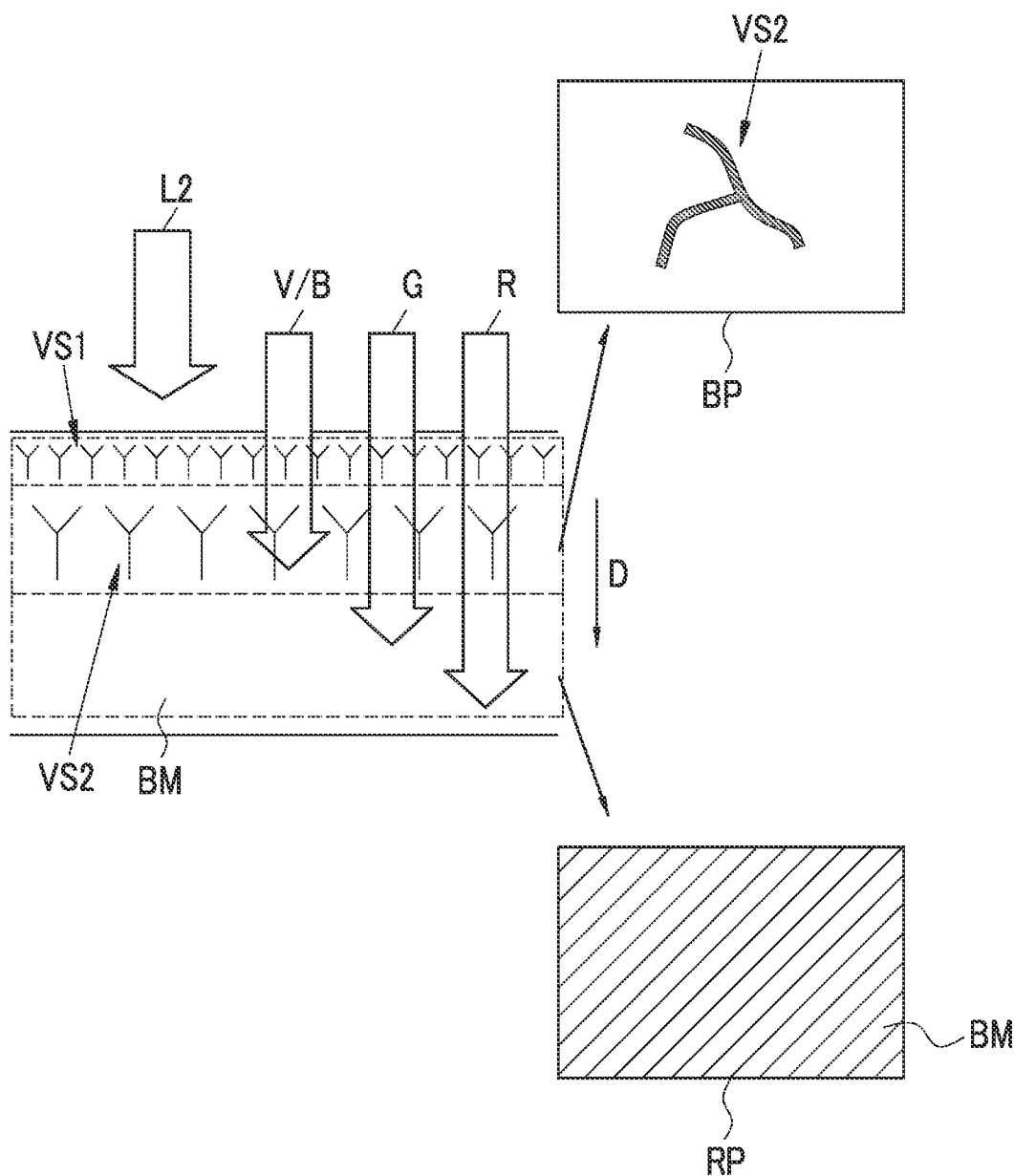
FIG. 15 is a diagram illustrating a violet-blue light image and a green-red light image that are obtained in a case where a subject is illuminated with the second illumination light.

An image in which the background mucous membrane BM and the deep blood vessels VS2 of the object to be observed are shown as shown in FIG. 14 is displayed by the second image. The second image is obtained on the basis of the second illumination light that includes violet light V, blue light B, green light G, and red light R. Green light G of the second illumination light L2 reaches a deep layer where the deep blood vessels VS2 are distributed as shown in FIG. 15. In FIG. 15, the object to be observed is illuminated with the second illumination light L2 from the upper side of the plane of paper and the lower side of the plane of paper corresponds to a depth direction D of the object to be observed. Since the light intensity of green light G is higher than the light intensity of each of blue light B, green light G, and red light R in the second illumination light L2, the image of the deep blood vessels VS2 included in a green light image GP obtained on the basis of the reflected light of green light G is emphasized. Here, since the light intensity of green light G is higher, a green light image GP is obtained. Further, red light R of the second illumination light L2 reaches the background mucous membrane BM that is distributed at a position deeper than the superficial blood vessels VS1 and the deep blood vessels VS2 (blood vessels present at positions deeper than the superficial blood vessels VS1). Accordingly, the image of the background mucous membrane BM is included in a red light image RP that is obtained on the basis of the reflected light of red light R. Since the second image is an image in which the red light image RP is combined as described above, the images of the background mucous membrane BM and the deep blood vessels VS2 are displayed.

As described above, in this embodiment, it is preferable that the first special observation image is generated by the first image signals, the second special observation image is generated by the second image signals, the superficial blood vessels are emphasized in the first special observation image, and medium-deep blood vessels present at positions deeper than the superficial blood vessels are emphasized in the second special observation image.

The detection unit 69 detects blood vessels or a lesion by the normal image, the first image, and the second image. Since the first image is an image in which the superficial blood vessels VS1 are shown, and the second image is an image in which the deep blood vessels VS2 are shown as described above, these blood vessels can be detected by image processing. Further, the detection unit 69 detects an abnormal portion of the first or second image, and regards the detected abnormal portion as abnormal image signals. The detection results of the blood vessels or the lesion are sent to the white balance unit 55 or the light source controller 21.

The display controller 64 performs control to display the normal image, the first image, and/or the second image, which are input from the normal observation image processing unit 62 or the special observation image processing unit 63, as images that can be displayed on the monitor 18. An image corresponding to each observation mode is displayed by the control of the display controller 64. In the case of the normal observation mode, the normal image is displayed on the monitor 18. Further, the first image (see FIG. 12) is displayed on the monitor 18 in the case of the first special observation mode. Furthermore, the second image (see FIG. 14) is displayed on the monitor 18 in the case of the second special observation mode.

Moreover, in the case of the multi-observation mode, the first image and the second image, which are color images, are switched and displayed on the monitor 18 according to the light emission period of the first illumination light and the light emission period of the second illumination light. That is, in a case where the first period is four frames and the second period is four frames, the first image continues to be displayed for four frames and the second image continues to be displayed for four frames.

As described above, two kinds of the first and second images can be automatically switched and displayed in the multi-observation mode without the operation of the mode changeover SW 13a that is performed by a user. Since the first and second images are automatically switched and displayed in this way, the same object to be observed is displayed in the first and second images as long as the object to be observed is not moved or the distal end part 12d of the endoscope 12 is not moved. However, since the spectral information of the first image and the spectral information of the second image are different from each other even in the case of the same object to be observed, the object to be observed looks different depending on a difference in spectral information. That is, the visibility of the superficial blood vessels is high in the first image, but the visibility of the deep blood vessels is high in the second image. Accordingly, since the first and second images are switched and displayed, the visibility of a plurality of blood vessels having different depths can be improved.

The normal observation mode, the first special observation mode, the second special observation mode, and the multi-observation mode where the first special observation mode and the second special observation mode are switched are provided in this embodiment. However, in addition to the normal observation mode and the multi-observation mode where the first special observation mode and the second special observation mode are switched, a plurality of observation modes different from these observation modes may be provided. In this case, a subject can be observed from more sides.

The static image-storage controller 66 performs control to store an image, which is obtained according to the instruction of the static image-acquisition instruction unit 13b at the timing of a static image-acquisition instruction, in the static image storage unit 65 as a static image. In the case of the normal observation mode, the static image-storage controller 66 stores a normal image, which is obtained at the timing of the static image-acquisition instruction, in the static image storage unit 65 as a static image. In the case of the first special observation mode, the static image-storage controller 66 stores a first special observation image, which is obtained at the timing of the static image-acquisition instruction, in the static image storage unit 65 as a static image. In the case of the second special observation mode, the static image-storage controller 66 stores a second special observation image, which is obtained at the timing of the static image-acquisition instruction, in the static image storage unit 65 as a static image. Further, in the case of the multi-observation mode, the static image-storage controller 66 stores a set of observation images for display, which is formed of the first special observation image and the second special observation image obtained at the timing of the static image-acquisition instruction, in the static image storage unit 65.

Next, the white balance processing will be described in detail below. The white balance unit 55 performs white balance processing using a corrected gain factor that is obtained through the correction of at least one of the first gain factor or the second gain factor. In a case where the first gain factor is corrected, a corrected first gain factor is used. In a case where the second gain factor is corrected, a corrected second gain factor is used. Correction may be to multiply a specific factor that is calculated using various data. The specific factor may be calculated whenever correction is performed, or a fixed period may be set and the specific factor may be calculated for each period.

Accordingly, since the corrected gain factor that is obtained through the correction of at least one of the first gain factor or the second gain factor is used as a gain factor, it is possible to provide an endoscope system that allows a user to easily recognize a difference between images while causing the brightness, tones, and the like of the respective images to match according to the change of a subject in a case where an image generated by the first image signals obtained using the first illumination light and an image generated by the second image signals obtained using the second illumination light are switched and displayed.

In this embodiment, the white balance unit 55 performs white balance processing using the second gain factor that is fixed and is not corrected. In this case, the first gain factor is corrected. Accordingly, it is possible to avoid that a normal mucous membrane and an inflamed mucous membrane are made to have the same tone in, for example, the first and second image signals due to a change in the tone of the second image signal. Moreover, the tone of the first image signal is made to match the tone of the second image signal. Therefore, since it is possible to maintain a difference between the tones of a normal mucous membrane and an inflamed mucous membrane and the like while maintaining a difference between the first and second image signals, a more correct diagnosis can be made.

In this embodiment, the first image signal or the second image signal includes a blue color signal, a red color signal, and a green color signal and the signal value of the first image signal or the signal value of the second image signal consists of a blue color signal value, a red color signal value, and a green color signal value. Further, the white balance unit 55 determines the first gain factor or the second gain factor for each of the blue color signal value, the red color signal value, and the green color signal value.

In a case where a first gain factor is to be corrected in this embodiment, a corrected first gain factor $AR_n$, which is obtained through the correction of a first gain factor used for first image signals of an acquisition period $P_{N-2}$ immediately before a certain acquisition period $P_N$ (N is an integer), is used as a first gain factor of the acquisition period $P_N$, which is used for first image signals included in a first image signal group of the acquisition period $P_N$. The acquisition period $P_N$ refers to a specific first period PL1 or a specific second period PL2. In this embodiment, the acquisition period $P_N$ is an acquisition period in which a first image signal group is acquired in a case where N is an odd number, and the acquisition period $P_N$ is an acquisition period in which a second image signal group is acquired in a case where N is an even number.

Figure 16:
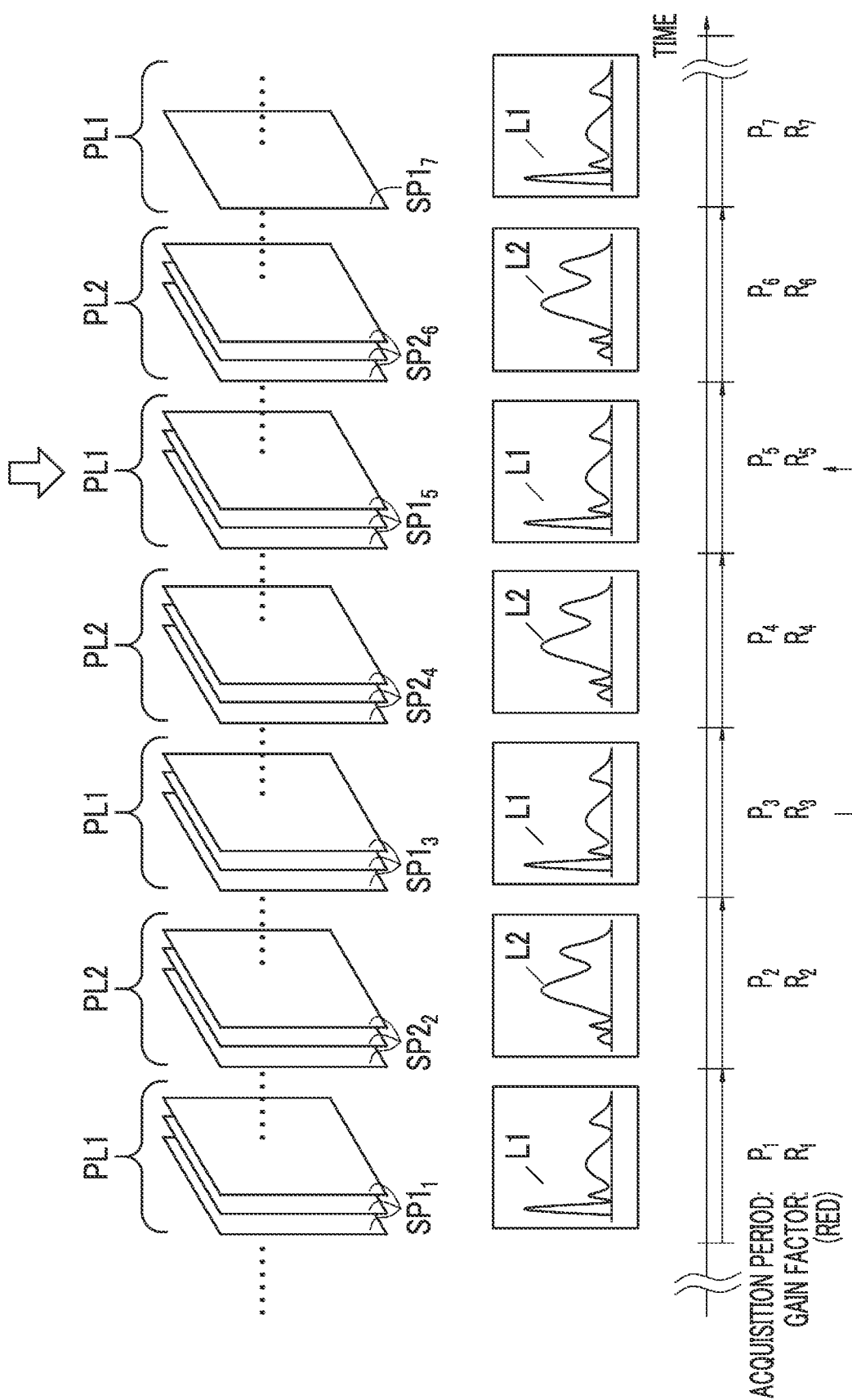
FIG. 16 is a diagram illustrating an example of a corrected first gain factor in an acquisition period $P_5$.

The corrected first gain factor $AR_n$ will be described using FIG. 16. A second period PL2 immediately before an acquisition period $P_5$, which is a certain first period PL1 indicated by an arrow of FIG. 16, is defined as an acquisition period $P_4$ and a first period PL1 immediately before the acquisition period $P_4$ is defined as an acquisition period $P_3$. An acquisition period $P_2$ and an acquisition period $P_1$ continue in order before the acquisition period $P_3$, and an acquisition period $P_6$ and an acquisition period $P_7$ continue in order after the acquisition period $P_5$. Since a first gain factor for red color signal values of first image signals $SP1_N$ included in the acquisition period $P_N$ is defined as a first gain factor $R_N$, a first gain factor for green color signal values thereof is defined as a first gain factor $G_N$, and a first gain factor for blue color signal values thereof is defined as a first gain factor $B_N$, a first gain factor for red color signal values of first image signals $SP1_5$ included in the acquisition period $P_5$ is a first gain factor $R_5$, a first gain factor for green color signal values thereof is a first gain factor $G_5$, and a first gain factor for blue color signal values thereof is a first gain factor $B_5$. Further, image signals, which are acquired in the acquisition period $P_N$ in a case where N is an odd number, are first image signals SPIN. Likewise, image signals, which are acquired in the acquisition period $P_N$ in a case where N is an even number, are second image signals $SP2_N$. The acquisition period $P_N$ is the first period PL1 in which a first image signal group is acquired in a case where N is an odd number, and is the second period PL2 in which a second image signal group is acquired in a case where N is an even number. The first gain factor $R_N$ for red color signal values will be mainly described below as a representative, but the same applies to the first gain factor $G_N$ for green color signal values and the first gain factor $B_N$ for blue color signal values.

A case where the first gain factor is to be corrected will be described. For example, in a case where N is 5, as shown by an arrow of FIG. 16, a corrected first gain factor $AR_5$, which is obtained through the correction of a first gain factor $R_3$ used for first image signals of an acquisition period $P_3$ in which first image signals are acquired immediately before an acquisition period $P_5$, is used for red color signal values in an acquisition period $P_N$ as the first gain factor $R_5$ of an acquisition period $P_5$ used for first image signals $SP1_5$ included in a first image signal group of the acquisition period $P_5$. A corrected gain factor $AR_N$ means a corrected gain factor $R_N$. Accordingly, in a case where the corrected gain factor $R_N$ is used as the gain factor $R_N$, the gain factor $R_N$ is the same as the corrected gain factor $AR_N$.

As described above, the same applies to each of a green color signal value and a blue color signal value. Accordingly, a corrected first gain factor $AG_5$, which is obtained through the correction of a first gain factor $G_3$ used for first image signals of the acquisition period $P_3$ in which first image signals are acquired immediately before the acquisition period $P_5$, is used for a green color signal value as a first gain factor $G_5$ of the acquisition period $P_5$ used for the first image signals $SP1_5$ included in the first image signal group of the acquisition period $P_5$. Further, a corrected first gain factor $AB_5$, which is obtained through the correction of a first gain factor $B_3$ used for first image signals of the acquisition period $P_3$ in which first image signals are acquired immediately before the acquisition period $P_5$, is used for a blue color signal value as a first gain factor $B_5$ of the acquisition period $P_5$ used for the first image signals $SP1_5$ included in the first image signal group of the acquisition period $P_5$.

Since corrected first gain factors $AR_N$, $AG_N$, and $AB_N$ are used for the first image signals $SP1_N$ acquired in the acquisition period $P_N$ as described above in a case where a subject is illuminated with a plurality of kinds of light while the plurality of kinds of light are switched and a plurality of images obtained through the illumination of the respective kinds of light are switched and displayed, images having stable tones and brightness can be obtained.

In this embodiment, a correction factor $W_N$ used to correct the first gain factor $R_N$ is used for the correction of the first gain factor $R_N$. The correction factor $W_N$ is calculated using a first calculation value that is obtained from calculation based on the first image signal group and a second calculation value that is obtained from calculation based on the second image signal group. The first calculation value represents a representative value of the signal values of the first image signal group, and the second calculation value represents a representative value of the signal values of the second image signal group. It is preferable that the correction factor $W_N$ is a ratio between the first and second calculation values. The details of the first and second calculation values and the correction factor $W_N$ will be described later. Even in a case where the second gain factor is to be corrected, the same correction factor may be used for correction.

A correction factor used to correct the first gain factor $R_N$ for red color signals is denoted by $Wr_N$, and correction factors for the first gain factor $G_N$ for green color signals and the first gain factor $B_N$ are denoted by $Wg_N$ and $Wb_N$, respectively. The corrected first gain factors $AR_N$, $AG_N$, and $AB_N$ in a case where first gain factors $R_{N-2}$, $G_{N-2}$, and $B_{N-2}$, which are used for first image signals of the acquisition period $P_{N-2}$ immediately before the acquisition period $P_N$, are corrected by being multiplied by the correction factors $Wr_N$, $Wg_N$, and $Wb_N$ are represented by the following equations (1) to (3).

$$AR_N = Wr_N \times R_{N-2} \quad (1)$$

$$AG_N = Wg_N \times G_{N-2} \quad (2)$$

$$AB_N = Wb_N \times B_{N-2} \quad (3)$$

Since the correction of the first gain factor $R_N$ is performed as described above, the first gain factor $R_N$ is corrected using the correction factor $Wr_N$ that is calculated using the first calculation value obtained from calculation based on the first image signal group and the second calculation value obtained from calculation based on the second image signal group. Accordingly, since the second period PL2 of the second illumination light L2 and the first period PL1 of the first illumination light L1 are adjusted together, it is possible to visualize a difference between images while causing the tints of the respective images to match according to the change of a subject in a case where the subject is illuminated with a plurality of kinds of light while the plurality of kinds of light are switched and a plurality of images obtained through the illumination of the respective kinds of light are switched and displayed.

Further, in this embodiment, in a case where the first gain factor $R_N$ is to be corrected, that is, in a case where the corrected first gain factor $AR_N$ having been subjected to correction processing is used as the first gain factor, the first gain factor $R_{N-K}$ of an acquisition period before an acquisition period $P_{N-2}$ may be used for correction in addition to a first gain factor $R_{N-2}$ used for first image signals of the acquisition period $P_{N-2}$ immediately before the acquisition period $P_N$.

More specifically, the first gain factor $R_N$ of the acquisition period $P_N$ may be a value of the sum of the respective products of first gain factors $R_{N-K}$ of a plurality of acquisition periods $P_{N-K}$ and weighting factors. K is an even number of 2 or more. It is preferable that the weighting factor is increased as an acquisition period is closer to the acquisition period $P_N$.

Furthermore, each of at least some of the first gain factors $R_{N-K}$ of the plurality of acquisition periods $P_{N-K}$ before the acquisition period $P_N$ is a corrected first gain factor $AR_{N-K}$ having been subjected to correction. It is preferable that the first gain factors of the plurality of acquisition periods $P_{N-K}$ are the first gain factors used for white balance processing in the respective acquisition periods $P_{N-K}$. Accordingly, since the corrected first gain factors $AR_{N-K}$ are used as the first gain factors $R_{N-K}$ in this case, the first gain factors $R_{N-K}$ and the corrected first gain factors $AR_{N-K}$ are equal to each other. In this embodiment, all the first gain factors $R_{N-K}$ of the plurality of acquisition periods $P_{N-K}$ before the acquisition period $P_N$ are the corrected first gain factors $AR_{N-K}$ having been subjected to correction processing, and the first gain factors $R_{N-K}$ used for white balance processing in the plurality of acquisition periods $P_{N-K}$ are the corrected first gain factors $AR_{N-K}$ having been subjected to correction processing.

Figure 17:
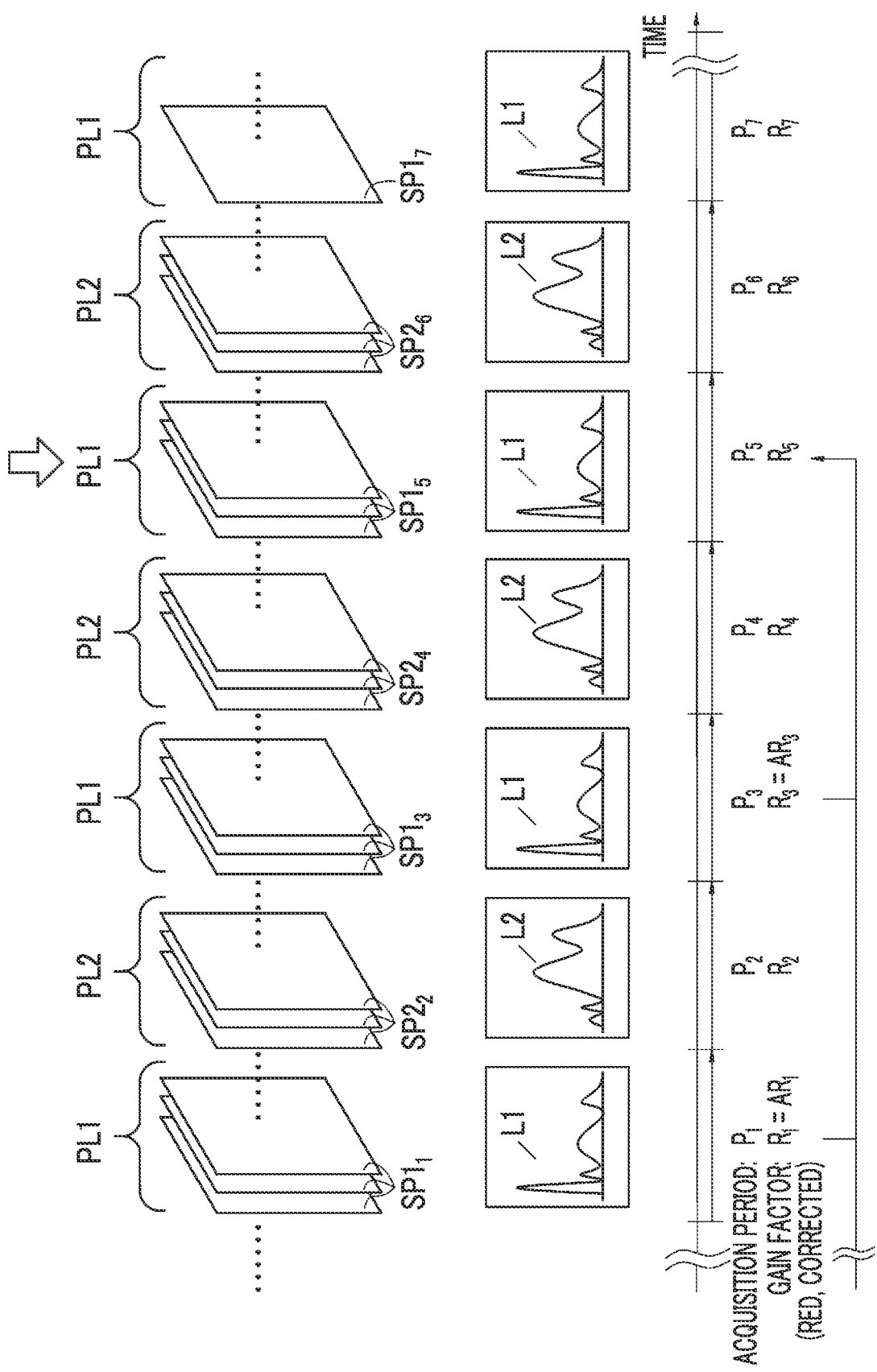
FIG. 17 is a diagram illustrating another example of the corrected first gain factor in the acquisition period $P_5$.

In a case where the first gain factor is to be corrected as described above and, for example, N is 5, as shown by an arrow of FIG. 17, a corrected first gain factor $AR_3$ that is a first gain factor used for first image signals SP1$3$ of an acquisition period $P_3$ immediately before an acquisition period $P_5$, a corrected first gain factor $AR_1$ that is a first gain factor used for first image signals SP1$_1$ of an acquisition period immediately before the previous acquisition period before the acquisition period $P_5$, and respective corrected first gain factors $AR_N$ and corrected first gain factors $AR_N$ of the plurality of acquisition periods $P_N$, which are used in a case where there are the acquisition periods $P_N$ in which first image signals SP1 are acquired before the acquisition period, are used for red color signal values in an acquisition period $P_N$ as the first gain factor $R_5$ of an acquisition period $P_5$ used for first image signals SP1$_5$ included in a first image signal group of the acquisition period $P_5$. The number of the corrected first gain factors $AR_N$ to be used is not particularly limited. Accordingly, although acquisition periods before the acquisition period $P_1$ are not shown, first gain factors $AR_{-1}$, $AR_{-3}$, . . . that are corrected first gain factors $AR_N$ used for first image signals SP1 of acquisition periods $P_{-1}$, $P_{-3}$, . . . are used in a case where, for example, there are the acquisition periods $P_{-1}$, $P_{-3}$, . . . before the acquisition period $P_1$.

It is preferable that the weighting factor is increased as an acquisition period is closer to the acquisition period $P_N$. Here, the weighting factors are denoted by $\alpha_n$ and the first gain factors $R_{N-K}$ (K is an even number of 2 or more) of the acquisition periods $P_{N-K}$ are sequentially denoted by reference numerals so that a weighting factor for a corrected first gain factor $AR_{N-2}$ of an acquisition period $P_{N-2}$ is denoted by $\alpha_1$ and a weighting factor for a corrected first gain factor $AR_{N-4}$ of an acquisition period $P_{N-4}$ is denoted by $\alpha_2$. The first gain factor $R_N$ of the acquisition period $P_N$ can be represented by the following equations (4) and (5). Here, N is an integer and n is a natural number.

$$R_N = \alpha_1 * AR_{N-2} + \alpha_2 * AR_{N-4} + \alpha_3 * AR_{N-6} \quad (4)$$

$$\Sigma \alpha_n = 1 \quad (5)$$

In a case where the weighting factors are attached as described above, the sum of all the weighting factors $\alpha_n$ is 1. In Equation (4), a corrected first gain factor $AR_{N-K}$ can be multiplied by a larger weighting factor $\alpha_n$ as an acquisition period is closer to the acquisition period $P_N$. Accordingly, for example, $\alpha_1$ is set to 0.5, $\alpha_2$ is set to 0.25, and $\alpha_3$ is set to 0.125, that is, the weighting factor is set to 0.5°. Therefore, Equation (5) can be satisfied with regard to $\alpha_n$.

In this embodiment, for example, in a case where the corrected first gain factor $AR_3$ of the acquisition period $P_3$ is weighted by the weighting factor $\alpha_1$, the corrected first gain factor $AR_1$ of the acquisition period $P_1$ is weighted by the weighting factor $\alpha_2$, and the corrected first gain factor of the acquisition period $P_{-1}$ is weighted by the weighting factor $\alpha_3$, the weighting factor is increased as an acquisition period is closer to the acquisition period $P_N$ so that $\alpha_1$ is 0.5, $\alpha_2$ is 0.25, $\alpha_3$ is 0.125, and the sum of $\alpha_4$ and the other weighting factors is 0.125.

Further, for example, in a case where the acquisition period $P_1$ is the first acquisition period $P_N$ in FIG. 17, the first gain factor $R_5$ used for the first image signals $SP1_5$ acquired in the acquisition period $P_5$ is represented by the following equation (6). $\alpha_1$ is 0.5 and $\alpha_2$ is 0.5.

$$R_5 = 0.5*AR_3 + 0.5*AR_1 \tag{6}$$

As described above, not only the gain factor $R_{N-2}$ for first image signals SP1 of the previous acquisition period $P_{N-2}$ but also the gain factor for a plurality of first image signals SP1 of an acquisition period before the previous acquisition period is used in order to calculate the first gain factor $R_N$ used for the first image signals $SP1_N$ of the acquisition period $R_N$. Accordingly, even though the tint or brightness of a subject is suddenly changed, the subject can be subsequently observed with the same tint or brightness without a significant change in a gain factor. Therefore, in a case where a subject is illuminated with a plurality of kinds of light while the plurality of kinds of light are switched and a plurality of images obtained through the illumination of the respective kinds of light are switched and displayed, images having stable tones and brightness can be obtained. The first gain factor has been mainly described in the above-mentioned embodiment. However, in a case where the second gain factor is to be corrected, the correction of the second gain factor can be performed in the same manner as the correction of the first gain factor.

In this embodiment, the first calculation values and the second calculation values may be used for the calculation of the correction factors. It is preferable that the first calculation values and the second calculation values used for the calculation of the correction factors are as follows. That is, the first calculation value is obtained from the arithmetic averaging of the respective first image signal value averages obtained from the averaging of the signal values of the first image signals SP1 in the first image signals SP1 included in the first image signal group, and the second calculation value is obtained from the arithmetic averaging of the respective second image signal value averages obtained from the averaging of the signal values of the second image signals SP2 in the second image signals SP2 included in the second image signal group. Values obtained from the first image signal group and the second image signal group can be used as the first calculation values and the second calculation values in addition to the arithmetic averages of the respective image signal value averages as described above. For example, values obtained from calculation processing, such as addition and averaging, of signal values of first image signals SP1 included in a first image signal group of a specific period in the past and signal values of second image signals SP2 included in a second image signal group of a specific period in the past may be used as the first calculation values and the second calculation values.

More specifically, for example, the correction factor-calculating unit 56 calculates the first image signal value averages, which are the averages of the signal values of the first image signals SP1, for the respective first image signals SP1 included in the first image signal group first by the number of the first image signals SP1. Then, values obtained from the arithmetic averaging of the respective plurality of first image signal value averages are used as the first calculation values. Further, likewise, the correction factor-calculating unit 56 also calculates the second image signal value averages, which are the averages of the signal values of the second image signals SP2, of the second image signals SP2 with regard to the respective second image signals SP2 included in the second image signal group by the number of the second image signals SP2. After that, values obtained from the arithmetic averaging of the respective plurality of second image signal value averages are used as the second calculation values.

Figure 18:
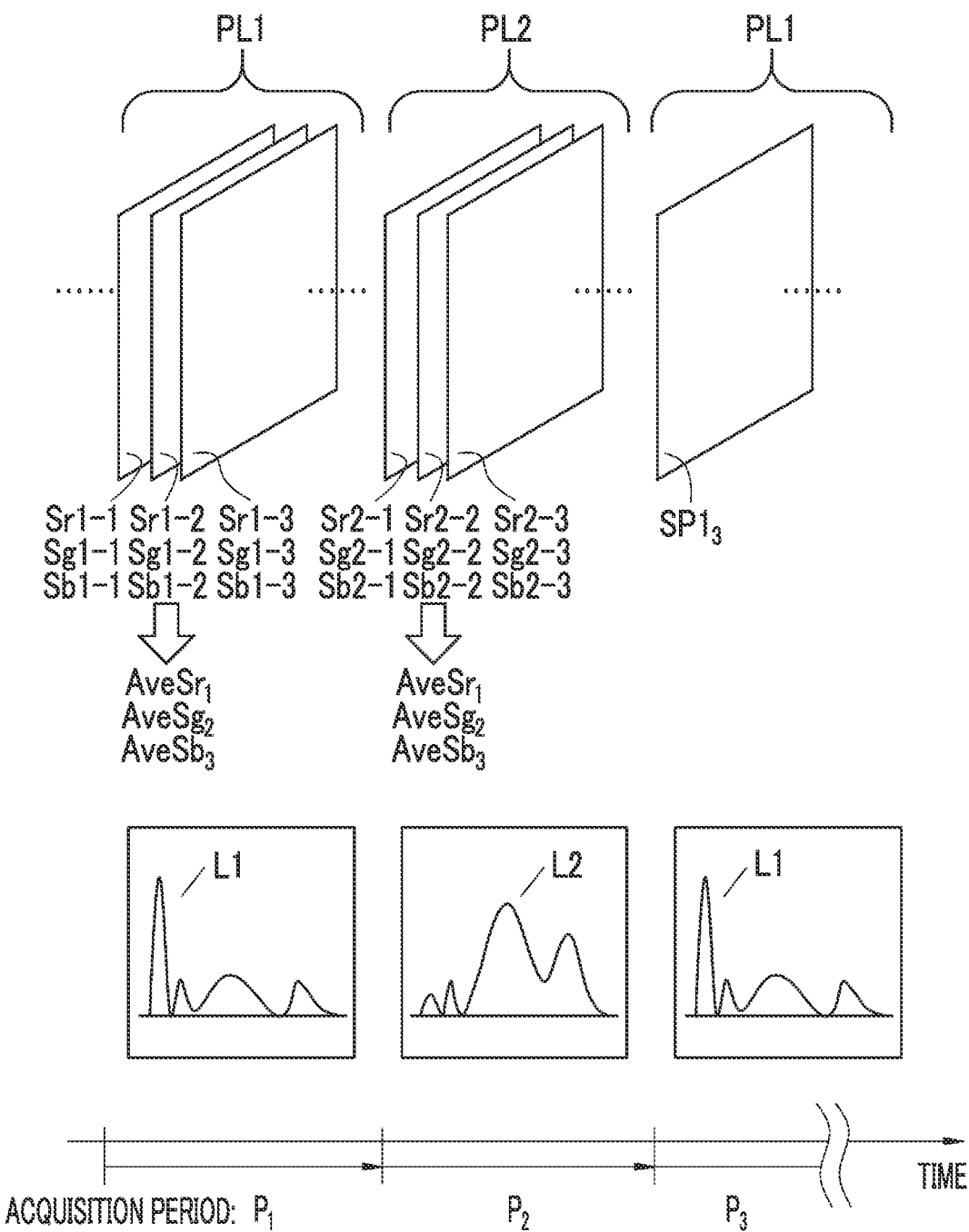
FIG. 18 is a diagram illustrating first image signal value averages and second image signal value averages.

The first calculation values and the second calculation values will be described with reference to FIG. 18. For example, in order to calculate the correction factor for the corrected gain factor $AR_N$ used for the first image signals SP13 included in the acquisition period $P_3$, the first calculation value and the second calculation value are calculated by calculation based on the image signals of the acquisition periods $P_1$ and $P_2$. First, RGB signal values of the first image signals are sequentially denoted by reference numerals so that RGB signal values of any one first image signal of the plurality of first image signals $SP1_1$ included in the acquisition period $P_1$ are denoted by $r_{1-1}$, $g_{1-1}$, and $b_{1-1}$, and RGB signal values of another first image signal are denoted by $r_{1-2}$, $g_{1-2}$, and $b_{1-2}$. Since the number of frames of the acquisition period $P_1$ is L, the number of the first image signals included in the acquisition period $P_1$ is L and the RGB signal values of the first image signals are denoted by $r_{1-1}$, $g_{1-1}$, and $b_{1-1}$ to $r_{1-L}$, $g_{1-L}$, and $b_{1-L}$.

Further, likewise, even with regard to a plurality of second image signals $SP2_2$ included in the acquisition period $P_2$, RGB signal values of any one second image signal of the plurality of second image signal $SP2_2$ included in the acquisition period are denoted by $r_{2-1}$, $g_{2-1}$, and $b_{2-1}$. Since the number of frames of the acquisition period $P_2$ is M, the number of the second image signals included in the acquisition period $P_2$ is M and the RGB signal values of the second image signals are denoted by $r_{2-1}$, $g_{2-1}$, and $b_{2-1}$ to $r_{2-M}$, $g_{2-M}$, and $b_{2-M}$.

Furthermore, the number of pixels of each image signal in a horizontal direction is i and the number of pixels thereof in a vertical direction is j. The first image signal value averages are the averages of the respective color signal values of the plurality of first image signals in an image plane, and are denoted by $Sr_{1-1}$, $Sg_{1-1}$, and $Sb_{1-1}$. Likewise, the second image signal value averages are the averages of the respective color signal values of the plurality of second image signals in an image plane, and are denoted by $Sr_{2-1}$, $Sg_{2-1}$, and $Sb_{2-1}$. Accordingly, $Sr_{1-1}$, $Sg_{1-1}$, $Sb_{1-1}$, $Sr_{2-1}$, $Sg_{2-1}$, and $Sb_{2-1}$ are obtained from the following equations (7) to (12). General equations are the following equations (13) to (18).

$$Sr_{1-1} = \frac{1}{i*j}\sum r_{1-1} \tag{7}$$

$$Sg_{1-1} = \frac{1}{i*j}\sum g_{1-1} \tag{8}$$

$$Sb_{1-1} = \frac{1}{i*j}\sum b_{1-1} \tag{9}$$

$$Sr_{2-1} = \frac{1}{i*j}\sum r_{2-1} \tag{10}$$

$$Sg_{2-1} = \frac{1}{i*j}\sum g_{2-1} \tag{11}$$

$$Sb_{2-1} = \frac{1}{i*j}\sum b_{2-1} \tag{12}$$

-continued $$Sr_{1-L} = \frac{1}{i*j}\sum r_{1-L} \qquad (13)$$

$$Sg_{1-L} = \frac{1}{i*j}\sum g_{1-L} \qquad (14)$$

$$Sb_{1-L} = \frac{1}{i*j}\sum b_{1-L} \qquad (15)$$

$$Sr_{2-M} = \frac{1}{i*j}\sum r_{2-M} \qquad (16)$$

$$Sg_{2-M} = \frac{1}{i*j}\sum g_{2-M} \qquad (17)$$

$$Sb_{2-M} = \frac{1}{i*j}\sum b_{2-M} \qquad (18)$$

Then, since the first calculation values are values obtained from the arithmetic averaging of the respective first image signal value averages, values obtained from the addition and averaging of all the first image signal value averages of the acquisition period $P_1$ with regard to the plurality of first image signals of which the number is the same as the number of frames included in the acquisition period $P_1$ are denoted by $AveSr_1$, $AveSg_1$, and $AveSb_1$, respectively. Accordingly, since there are L first image signal value averages $Sr_{1-1}$ to of the acquisition period $P_1$, the first calculation values are value that are obtained by dividing the sums of these L first image signal value averages by L. These first calculation values are obtained from the following equations (19) to (21). Likewise, since the second calculation values are values obtained from the arithmetic averaging of the respective second image signal value averages, values obtained from the addition and averaging of all the second image signal value averages of the acquisition period $P_2$ with regard to the plurality of second image signals of which the number is the same as the number of frames included in the acquisition period $P_2$ are denoted by $AveSr_2$, $AveSg_2$, and $AveSb_2$, respectively. In this case, these second calculation values are obtained from the following equations (22) to (24).

$$AveSr_1 = \frac{1}{L}\sum Sr_{1-L} \qquad (19)$$

$$AveSg_1 = \frac{1}{L}\sum Sg_{1-L} \qquad (20)$$

$$AveSb_1 = \frac{1}{L}\sum Sb_{1-L} \qquad (21)$$

$$AveSr_2 = \frac{1}{M}\sum Sr_{2-M} \qquad (22)$$

$$AveSg_2 = \frac{1}{M}\sum Sg_{2-M} \qquad (23)$$

$$AveSb_2 = \frac{1}{M}\sum Sb_{2-M} \qquad (24)$$

Here, for example, in a case where a correction factor for a gain factor for a red color signal is denoted by $Wr_3$, a correction factor for a gain factor for a green color signal is denoted by $Wg_3$, and a correction factor for a gain factor for a blue color signal is denoted by $Wb_3$ with regard to a correction factor $W_3$ of the acquisition period $P_3$, these correction factors $Wr_3$, $Wg_3$, and $Wb_3$ are calculated using $AveSr_1$, $AveSg_1$, and $AveSb_1$ that are the first calculation values of the acquisition period $P_1$ and $AveSr_2$, $AveSg_2$, and $AveSb_2$ that are second calculation values of the acquisition period $P_2$. In this embodiment, the calculation values and the correction factors correspond to the same color so that the correction factor $Wr_3$ for a red color signal is calculated using the first calculation value $AveSr_1$ for a red color signal and the second calculation value $AveSr_2$ for a red color signal. In some cases, correction factors may be calculated using a combination other than the same color.

In a case where the first image signal value averages or the second image signal value averages are to be calculated, it is preferable that the detection unit 69 calculates the first image signal value averages or the second image signal value averages after determining image signals, which correspond to portions detected as blood vessels or lesions, as abnormal image signals and removing the image signals in the first image signals or the second image signals. Likewise, it is preferable that the detection unit 69 calculates the first image signal value averages or the second image signal value averages after determining image signals, which correspond to portions detected as abnormal pixels, as abnormal image signals and removing the image signals in the first image signals or the second image signals. Here, the abnormal pixels include dark portions, bright portions of a halation and the like, abnormal frames, or the like.

The first calculation values or the second calculation values are calculated as described above, so that correction factors are calculated using the respective signal values of the entire image in the first image signal and the second image signals. Accordingly, in a case where a plurality of images obtained through the illumination of the respective kinds of light are switched and displayed, it is possible to prevent the tint, the brightness, and the like of the entire image from being suddenly changed according to the change of a subject and to display the plurality of image. Therefore, a user easily recognizes a difference between the plurality of images. In a case where correction factors are calculated using the signal values of the image from which the respective abnormal image signals are removed in the first image signals and the second image signals, the plurality of images can be displayed with more stable tones and brightness.

In a case where a ratio between the first and second calculation values is used as a correction factor in this embodiment, the correction factor is obtained as follows. That is, a value of the product of a first gain factor, which is used for first image signals included in a first image signal group of an acquisition period $P_{N-2}$, and the value of a ratio between a first calculation value of the acquisition period $P_{N-2}$ and a second calculation value of an acquisition period $P_{N-1}$ can be used as a first gain factor of the acquisition period $P_N$.

Figure 19:
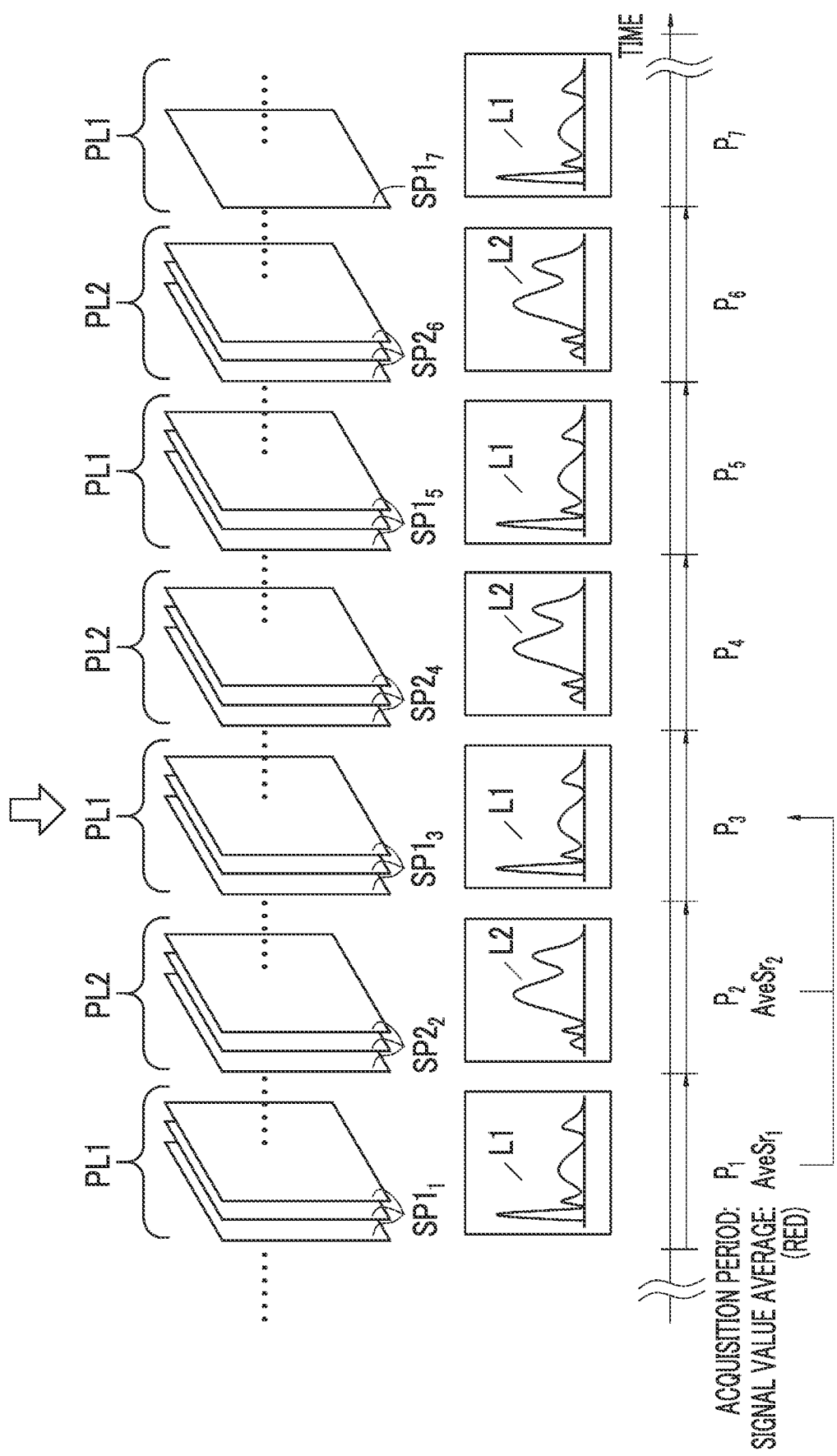
FIG. 19 is a diagram illustrating an example of a correction factor.

For example, as shown in FIG. 19, the correction factors $Wr_3$, $Wg_3$, and $Wb_3$ of the acquisition period $P_3$ are represented by the following equations (25) to (27) in a case where $AveSr_1$, $AveSg_1$, $AveSb_1$, $AveSr_2$, $AveSg_2$, and $AveSb_2$ are used as the first and second calculation values.

$$Wr_3 = \frac{AveSr_2}{AveSr_1} \qquad (25)$$

$$Wg_3 = \frac{AveSg_2}{AveSg_1} \qquad (26)$$

-continued $$Wb_3 = \frac{AveSb_2}{AveSb_1} \quad (27)$$

Accordingly, in a case where the corrected first gain factors $AR_3$, $AG_3$, and $AB_3$, which are corrected gain factors, are used as the gain factors $R_3$, $G_3$, and $B_3$, which correspond to the respective colors, of the acquisition period $P_3$, the following equations (28) to (30) can be obtained from Equations (1) to (3) and Equations (25) to (27).

$$R_3 = \frac{AveSr_2}{AveSr_1} R_1 \quad (28)$$

$$G_3 = \frac{AveSg_2}{AveSg_1} G_1 \quad (29)$$

$$B_3 = \frac{AveSb_2}{AveSb_1} B_1 \quad (30)$$

Equations (28) to (30) are equations relating to the gain factors of the acquisition period $P_3$, but the following equations (31) to (33) can be obtained in a case where these equations are generalized. In the following equations (31) to (33), h is an odd number. Accordingly, corrected first gain factors $AR_{h+2}$, $AG_{h+2}$, and $AB_{h+2}$ for a first image of an acquisition period (h+2), which is obtained using the first illumination light, are obtained from the following equations (31) to (33).

$$R_{h+2} = \frac{AveS_{rh+1}}{AveS_{r1}} R_h \quad (31)$$

$$G_{h+2} = \frac{AveS_{gh+1}}{AveS_{g1}} G_h \quad (32)$$

$$B_{h+2} = \frac{AveS_{bh+1}}{AveS_{b1}} B_h \quad (33)$$

Figure 20:
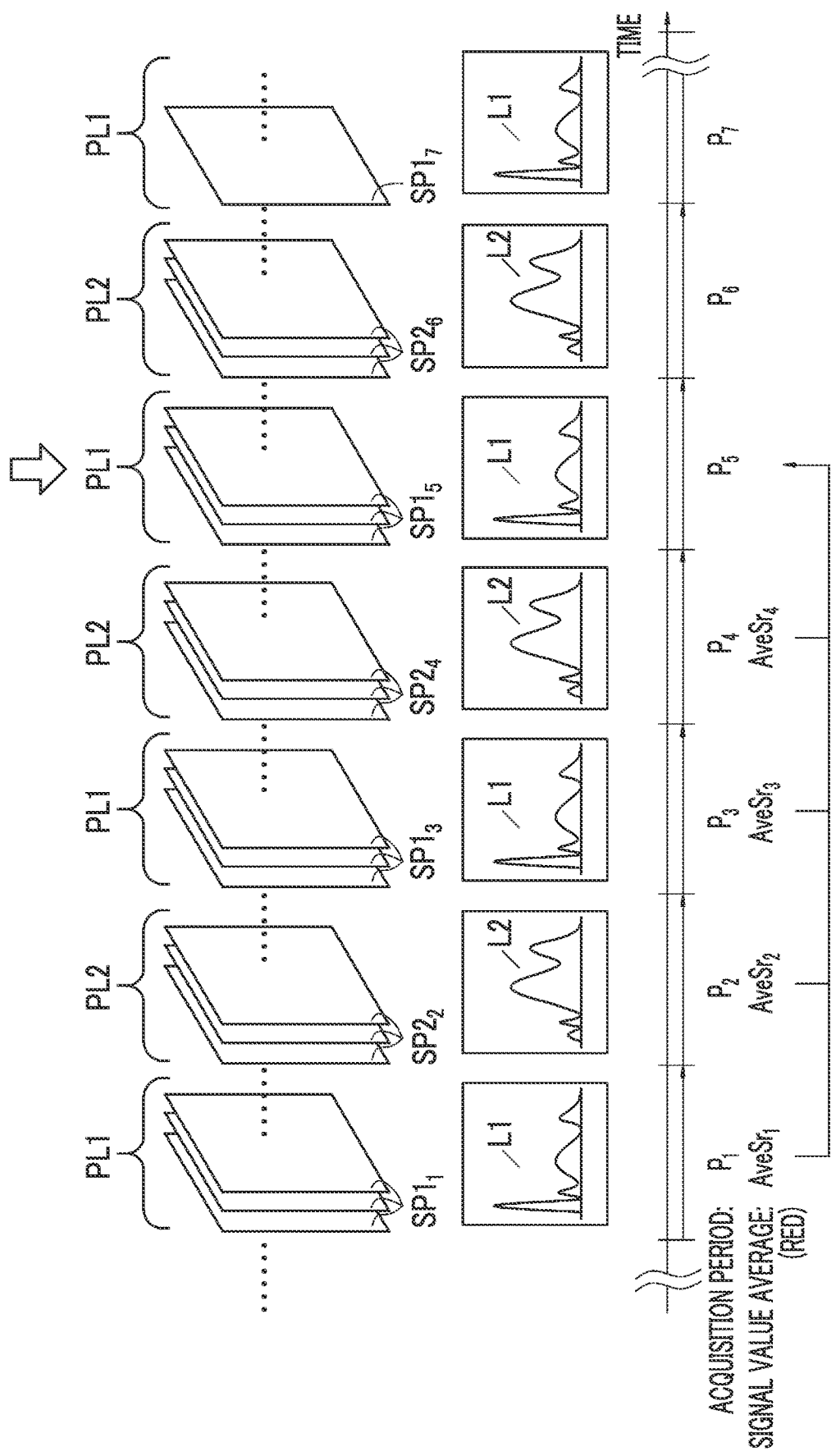
FIG. 20 is a diagram illustrating another example of the correction factor.

Further, in a case where the first gain factor $R_N$ of the acquisition period $P_N$ is a value of the sum of the respective products of first gain factors $R_{N-K}$ of a plurality of acquisition periods $P_{N-K}$ and weighting factors as shown in FIG. 20, a corrected first gain factor can be represented by the following equation (34) from Equation (4) and Equations (31) to (33). Here, the first gain factor is used as a first gain factor of an acquisition period h. Here, K is an even number of 2 or more.

$$R_h = \quad (34)$$
$$\alpha_1 * \frac{AveSr_{h-1}}{AveSr_{h-2}} R_{h-2} + \alpha_2 * \frac{AveSr_{h-3}}{AveSr_{h-4}} R_{h-4} + \alpha_3 * \frac{AveSr_{h-5}}{AveSr_{h-6}} R_{h-6} \ldots$$

In Equation (34), the sum of all the factors a is 1 as described above, and the corrected first gain factor is set to a larger factor as an acquisition period is closer to the acquisition period h. Accordingly, for example, $\alpha_1$ is set to 0.5, $\alpha_2$ is set to 0.25, and $\alpha_3$ is set to 0.125, that is, the weighting factor is set to 0.5'. Therefore, Equation (5) can be satisfied with regard to $\alpha_n$.

$$\Sigma \alpha_n = 1 \quad (5)$$

As described above, for example, not only the gain factor for a first image of the previous acquisition period but also the gain factor for a first image of an acquisition period before the previous acquisition period is used in order to calculate the first gain factor. Accordingly, even though the tint or brightness of a subject is suddenly changed, the subject can be subsequently observed with the same tint or brightness without a significant change in a gain factor. The first gain factor has been mainly described in the above-mentioned embodiment, but the calculation of the second gain factor can also be performed in the same manner as described above.

Since the correction factor is calculated using the previous first and second calculation values as described above, the gain factor can be corrected according to the change of a subject. Accordingly, it is possible to visualize a difference between images while causing the tints of the respective images to match according to the change of a subject better.

It is preferable that the first gain factors $R_N$, $G_N$, and $B_N$ of the acquisition period $P_N$ are not corrected in a case where differences between first gain factors $R_N$, $G_N$, and $B_N$ of an acquisition period $P_N$ and first gain factors $R_{N-2}$, $G_{N-2}$, and $B_{N-2}$ used for first image signals included in a first image signal group of an acquisition period $P_{N-2}$ are equal to or smaller than preset threshold values. Further, it is preferable that the first gain factors $R_N$, $G_N$, and $B_N$ of the acquisition period $P_N$ are not corrected in a case where differences between the first gain factors $R_N$, $G_N$, and $B_N$ of the acquisition period $P_N$ and the first gain factors $R_{N-2}$, $G_{N-2}$, and $B_{N-2}$ used for first image signals included in a first image signal group of the acquisition period $P_{N-2}$ are equal to or larger than the preset threshold values. Here, the case where the differences are equal to or smaller than the preset threshold values is, for example, a case where the image signals include abnormal pixel portions, such as a dead zone, and the like. Here, the dead zone is a portion of an acquired image where illumination light does not reach, a portion thereof outside the lens, and the like. Further, the case where the differences are equal to or larger than the preset threshold values is, for example, a case where the image signals include abnormal pixel portions, such as a halation, and the like. These abnormal pixel portions of the image signals are detected by the detection unit 69.

The light source controller 21 emits each illumination light according to a preset light amount ratio in the above-mentioned embodiment, but may control a light amount ratio on the basis of the first gain factor or the second gain factor and may emit each illumination light. That is, the first illumination light may include violet light, blue light, green light, and red light; the second illumination light may include violet light, blue light, green light, and red light; and the light source controller 21 may control the amount of each color light, which is included in the first illumination light and the second illumination light, to be emitted on the basis of the first gain factor or the second gain factor.

The light source controller 21 controls the respective LEDs 20a to 20d for the first illumination light so that the first illumination light of which the light intensity ratios of violet light V, blue light B, green light G, and red light R are Vs1:Bs1:Gs1:Rs1 is emitted. As a result, R signal values of the first image, G signal values of the first image, and B signal values of the first image are obtained. However, in a case where, for example, corrected first gain factors are calculated as $AR_1$, $AG_1$, and $AB_1$, the light intensity ratio of the first illumination light may be controlled so that the R signal values of the values of the products of the first image signal values and the respective corrected first gain factors $AR_N$, $AG_N$, and $AB_N$ are obtained in a case where gain processing is not performed. The light intensity ratio of the first illumination light can be controlled in the same manner as described above with regard to even the G signal values of the first image and the B signal values of the first image.

It is preferable that the light source controller 21 increases the amount of light to be emitted up to the preset minimum amount of light to be emitted in a case where the amount of light to be emitted controlled on the basis of the corrected first gain factor or the corrected second gain factor as described above is equal to or smaller than a specific threshold value. For example, the light source controller 21 controls the amount of light to be emitted to the amount of light to be emitted where an image signal value subjected to white balance processing using a first gain factor reaches the same image signal value in a case where white balance processing is not performed, but compares the amount of light to be emitted in this case with a specific threshold value.

There is a case where noise is generated in a processed image due to gain processing. However, since the light source controller 21 adjusts a light amount ratio in this way, it is possible to obtain an image of which the tint or brightness is adjusted while suppressing the generation of noise caused by gain processing.

Figure 21:
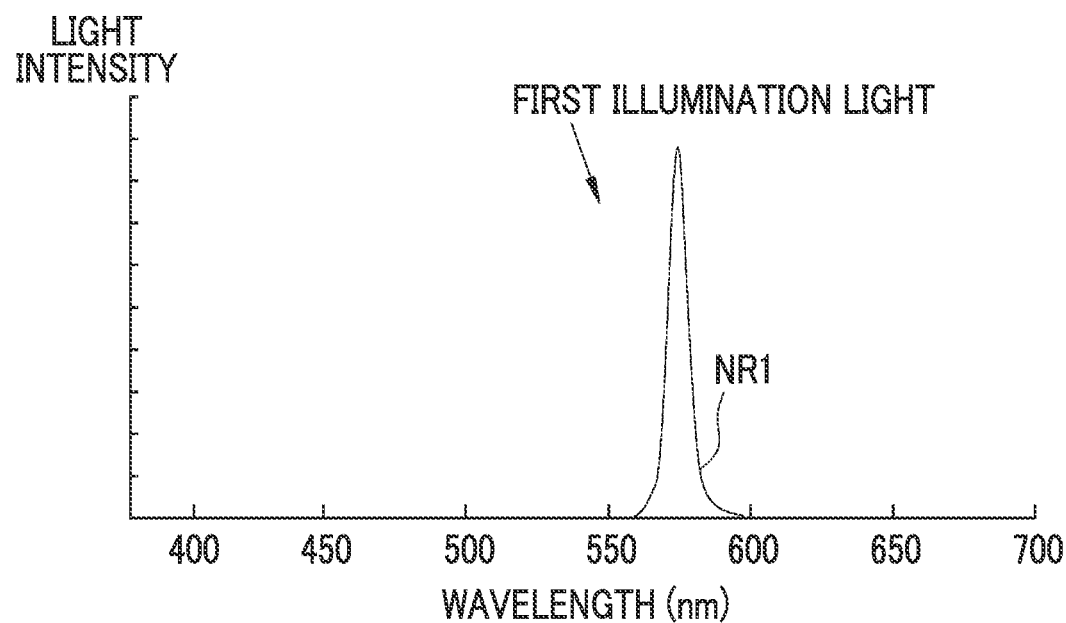
FIG. 21 is a graph showing the emission spectrum of first illumination light including first red narrow-band light.
Figure 22:
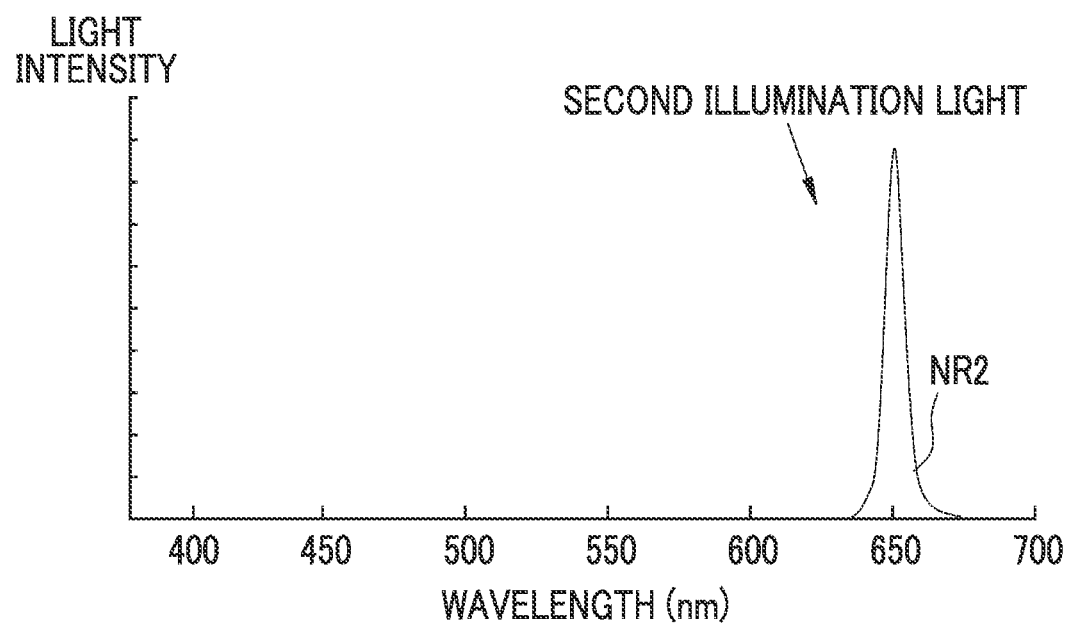
FIG. 22 is a graph showing the emission spectrum of second illumination light including second red narrow-band light.

As in the above-mentioned embodiment, the first illumination light may include first red narrow-band light NR1 of which the central wavelength or the peak wavelength is in the range of 560 to 580 nm as shown in FIG. 21 instead of violet light V, blue light B, green light G, and red light R. Further, the second illumination light may include second red narrow-band light NR2 of which the central wavelength or the peak wavelength is in the range of 630 to 670 nm as shown in FIG. 22 instead of violet light V, blue light B, green light G, and red light R. In this case, it is preferable that specific light amount conditions (the light amount condition of the first red narrow-band light NR1 and the light amount condition of the second red narrow-band light NR2) are determined so that the signal value of a first red color signal (first specific color signal) for specific biological tissue corresponding to at least specific biological tissue among first image signals obtained in a case where the image of an object to be observed is picked up using the first red narrow-band light NR1 is equal to the signal value of a second red color signal (second specific color signal) for specific biological tissue corresponding to at least the specific biological tissue among second image signals obtained in a case where the image of the object to be observed is picked up using the second red narrow-band light NR2. Each of the first red narrow-band light NR1 and the second red narrow-band light NR2 has sensitivity to the R-pixel of the image pickup sensor 48.

The hardware structures of the processing units included in the processor device 16 in the above-mentioned embodiment, such as the image acquisition unit 52, the DSP 54, the noise removing unit 58, the normal observation image processing unit 62, the special observation image processing unit 63, the display controller 64, the static image storage unit 65, and the static image-storage controller 66, are various processors to be described below. The various processors include: a central processing unit (CPU) that is a general-purpose processor functioning as various processing units by executing software (program); a graphical processing unit (GPU); a programmable logic device (PLD) that is a processor of which circuit configuration can be changed after manufacture, such as a field programmable gate array (FPGA); a dedicated electrical circuit that is a processor having circuit configuration designed exclusively to perform specific processing, such as an application specific integrated circuit (ASIC); and the like.

One processing unit may be formed of one of these various processors, or may be formed of a combination of two or more same kind or different kinds of processors (for example, a plurality of FPGAs, a combination of a CPU and an FPGA, or a combination of a GPU and a CPU). Further, a plurality of processing units may be formed of one processor. As an example where a plurality of processing units are formed of one processor, first, there is an aspect where one processor is formed of a combination of one or more CPUs and software as typified by a computer, such as a client or a server, and functions as a plurality of processing units. Second, there is an aspect where a processor fulfilling the functions of the entire system, which includes a plurality of processing units, by one integrated circuit (IC) chip as typified by System On Chip (SoC) or the like is used. In this way, various processing units are formed of one or more of the above-mentioned various processors as hardware structures.

In addition, the hardware structures of these various processors are more specifically electrical circuitry where circuit elements, such as semiconductor elements, are combined.

The invention can be applied to a processor device, which is combined with a capsule endoscope system, or various medical image processing devices in addition to the processor device that is combined with the endoscope system described in the above-mentioned embodiment.

The invention can also be embodied by another embodiment to be described below.

A processor device of an endoscope system including a light source unit that emits first illumination light and second illumination light having an emission spectrum different from an emission spectrum of the first illumination light, in which control to automatically switch and emit the first illumination light and the second illumination light is performed, and each of a light emission period in which the first illumination light is emitted and a light emission period in which the second illumination light is emitted is a light emission period of at least one or more frames, a first image signal group including a first image signal obtained from image pickup of a subject illuminated with the first illumination light in the light emission period of the first illumination light and a second image signal group including a second image signal obtained from image pickup of the subject illuminated with the second illumination light in the light emission period of the second illumination light are acquired, the first image signal is multiplied by a first gain factor and the second image signal is multiplied by a second gain factor to perform white balance processing, and a white balance unit performs the white balance processing using a corrected gain factor that is obtained through correction of at least one of the first gain factor or the second gain factor.

EXPLANATION OF REFERENCES

10: endoscope system
12: endoscope
12a: insertion part
12b: operation part
12c: bendable part
12d: distal end part
12e: angle knob 13a: mode changeover SW
13b: static image-acquisition instruction unit
14: light source device
16: processor device
18: monitor
19: user interface
20: light source unit
20a: violet light emitting diode (V-LED)
20b: blue light emitting diode (B-LED)
20c: green light emitting diode (G-LED)
20d: red light emitting diode (R-LED)
21: light source controller
23: optical path-combination unit
24: light emission period-setting unit
26a: slide bar
26b: slide bar
27a: slider
27b: slider
30a: illumination optical system
30b: image pickup optical system
41: light guide
45: illumination lens
46: objective lens
48: image pickup sensor
48b: B-filter
48g: G-filter
48r: R-filter
50: CDS/AGC circuit
52: image acquisition unit
54: digital signal processor (DSP)
55: white balance unit
56: correction factor-calculating unit
58: noise removing unit
60: signal switching unit
62: normal observation image processing unit
63: special observation image processing unit
64: display controller
65: static image storage unit
66: static image-storage controller
67: first special observation image processing unit
68: second special observation image processing unit
69: detection unit
L1: first illumination light
L2: second illumination light
PL1: first period
PL2: second period
SP1: first special observation image (first image)
SP2: second special observation image (second image)
VP: violet light image
RP: red light image
VS1: superficial blood vessel
VS2: deep blood vessel
BM: background mucous membrane
V/B: violet light and blue light
G: green light
R: red light
D: depth direction

What is claimed is:

1. An endoscope system comprising:
a light source that emits first illumination light and second illumination light having an emission spectrum different from an emission spectrum of the first illumination light;
a light source controller that performs control to automatically switch and emit the first illumination light and the second illumination light and each of a light emission period in which the first illumination light is emitted and a light emission period in which the second illumination light is emitted is a light emission period of at least one or more frames; and
a processor configured to function as:
an image acquisition unit that acquires a first image signal group including a first image signal obtained from image pickup of a subject illuminated with the first illumination light in the light emission period of the first illumination light and a second image signal group including a second image signal obtained from image pickup of the subject illuminated with the second illumination light in the light emission period of the second illumination light; and
a white balance unit that multiplies the first image signal by a first gain factor and multiplies the second image signal by a second gain factor to perform white balance processing,
wherein the white balance unit performs the white balance processing using a corrected gain factor that is obtained through correction of at least one of the first gain factor or the second gain factor,
a correction factor used to correct at least one of the first gain factor or the second gain factor is used for the correction of the first gain factor or the second gain factor,
the correction factor is calculated using a first calculation value obtained from calculation based on the first image signal group and a second calculation value obtained from calculation based on the second image signal group,
the first calculation value is obtained from arithmetic averaging of respective first image signal value averages obtained from averaging of signal values of the first image signals in the first image signals included in the first image signal group, and
the second calculation value is obtained from arithmetic averaging of respective second image signal value averages obtained from averaging of signal values of the second image signals in the second image signals included in the second image signal group.

2. The endoscope system according to claim 1,
wherein the white balance unit performs the white balance processing using the second gain factor that is fixed and is not corrected.

3. The endoscope system according to claim 1,
wherein the first image signal or the second image signal includes a blue color signal, a red color signal, and a green color signal, and
a signal value of the first image signal or a signal value of the second image signal consists of a blue color signal value, a red color signal value, and a green color signal value.

4. The endoscope system according to claim 3,
wherein the white balance unit determines the first gain factor or the second gain factor for each of the blue color signal value, the red color signal value, and the green color signal value.

5. The endoscope system according to claim 1,
wherein, in a case where the first gain factor is to be corrected, each of at least some of the first gain factors of a plurality of acquisition periods $P_{N-K}$ (K is an even number of 2 or more) before an acquisition period $P_N$ used for the first image signals included in the first image signal groups of the plurality of acquisition periods $P_{N-K}$ is the corrected gain factor having been subjected to correction, the first gain factor of the acquisition period $P_N$ used for the first image signal included in the first image signal group of the acquisition period $P_N$ is a value of a sum of respective products of the first gain factors of the plurality of acquisition periods $P_{N-K}$ and weighting factors, and the weighting factor is larger as an acquisition period is closer to the acquisition period $P_N$.

6. The endoscope system according to claim 5,
wherein the first gain factors of the plurality of acquisition periods $P_{N-K}$ are used for the white balance processing in the respective acquisition periods $P_{N-K}$.

7. The endoscope system according to claim 1,
wherein the processor further configured to function as a detection unit that detects an image signal of a blood vessel or a lesion portion in the first image signals or the second image signals and regards the detected image signal as an abnormal image signal, and
wherein the first image signal value average or the second image signal value average is obtained using the signal values of the first image signals or the signal values of the second image signals except for the abnormal image signal, respectively.

8. The endoscope system according to claim 1,
wherein the processor further configured to function as a detection unit that detects an image signal of an abnormal pixel portion in the first image signals or the second image signals and regards the detected abnormal pixel portion as an abnormal image signal, and
wherein the first image signal value average or the second image signal value average is obtained using the signal values of the first image signals or the signal values of the second image signals except for the abnormal image signal, respectively.

9. The endoscope system according to claim 1,
wherein the correction factor is a ratio between the first and second calculation values.

10. The endoscope system according to claim 1,
wherein the first illumination light includes violet light, green light, and red light and the second illumination light includes blue light, green light, and red light, and
the light source controller controls an amount of each color light, which is included in the first illumination light and the second illumination light, to be emitted on a basis of the first gain factor or the second gain factor.

11. The endoscope system according to claim 10,
wherein the light source controller increases the amount of light to be emitted up to a preset minimum amount of light to be emitted in a case where the amount of light to be emitted controlled on the basis of the first gain factor or the second gain factor is equal to or smaller than a specific threshold value.

12. The endoscope system according to claim 1,
wherein the image processing unit generates a first observation image for display by the first image signal and generates a second observation image for display by the second image signal, and
a superficial blood vessel is emphasized in the first observation image for display and a medium-deep blood vessel present at a position deeper than the superficial blood vessel is emphasized in the second observation image for display.

13. The endoscope system according to claim 1,
wherein, in a case where the first gain factor is to be corrected, the first gain factor of an acquisition period $P_N$ (N is an integer) used for the first image signal included in the first image signal group of the acquisition period $P_N$ is a corrected first gain factor that is obtained through correction of the first gain factor of an acquisition period $P_{N-2}$ immediately before the acquisition period $P_N$ used for the first image signal of the acquisition period $P_{N-2}$.

14. The endoscope system according to claim 13,
wherein the first gain factor of the acquisition period $P_N$ is a value of a product of the first gain factor, which is used for the first image signal included in the first image signal group of the acquisition period $P_{N-2}$, and a value of a ratio between the first calculation value of the acquisition period $P_{N-2}$ and the second calculation value of an acquisition period $P_{N-1}$ immediately before the acquisition period $P_N$.

15. The endoscope system according to claim 13,
wherein the first gain factor of the acquisition period $P_N$ is not corrected in a case where a difference between the first gain factor of the acquisition period $P_N$ and the first gain factor used for the first image signal included in the first image signal group of the acquisition period $P_{N-2}$ is equal to or smaller than a preset threshold value.

16. The endoscope system according to claim 13,
wherein the first gain factor of the acquisition period $P_N$ is not corrected in a case where a difference between the first gain factor of the acquisition period $P_N$ and the first gain factor used for the first image signal included in the first image signal group of the acquisition period $P_{N-2}$ is equal to or larger than a preset threshold value.

* * * * *